US011203759B2

(12) United States Patent
Kiley et al.

(10) Patent No.: US 11,203,759 B2
(45) Date of Patent: Dec. 21, 2021

(54) OXYGEN-RESPONSIVE BACTERIAL GENE SWITCH

(71) Applicant: Wisconsin Alumni Research Foundation, Madison, WI (US)

(72) Inventors: Patricia J. Kiley, Middleton, WI (US); Dan M. Park, Dublin, CA (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 525 days.

(21) Appl. No.: 15/698,302

(22) Filed: Sep. 7, 2017

(65) Prior Publication Data

US 2018/0010138 A1 Jan. 11, 2018

Related U.S. Application Data

(63) Continuation of application No. 14/597,466, filed on Jan. 15, 2015, now abandoned.

(60) Provisional application No. 61/928,292, filed on Jan. 16, 2014.

(51) Int. Cl.
*C12N 15/70* (2006.01)
*C12N 15/63* (2006.01)

(52) U.S. Cl.
CPC ............. *C12N 15/70* (2013.01); *C12N 15/63* (2013.01)

(58) Field of Classification Search
CPC ................................ C12N 15/70; C12N 15/63
See application file for complete search history.

(56) References Cited

U.S. PATENT DOCUMENTS

2003/0162271 A1 8/2003 Zhang et al.

OTHER PUBLICATIONS

Sakai et al., Plant J., 66:796-805 (Year: 2011).*
Srinivasan et al., Nuc. Acids Res., 32(1) D421-D422 (Year: 2004).*
Sakai et al. (2011) Distinct evolutionary patterns of Oryza glaberrima deciphered by genome sequencing and comparative analysis. The Plant Journal, 66:796-805 (Year: 2011).*
Srinivasan et al. (2004) AppaDB: an AcedB database for the nematode satellite organism Pristionchus pacificus. Nucleic Acids Research, 32(1):D421-D422 (Year: 2004).*
Cox et al. (2007) Programming gene expression with combinatorial promoters. Molecular Systems Biology, 3(145):pp. 1-11 (Year: 2007).*
Chao et al. (1997) Aerobic Regulation of Isocitrate Dehydrogenase Gene (icd) Expression in *Escherichia coli* by the arcA and fnr Gene Products. Journal of Bacteriology, 179(13):4299-4304 (Year: 1997).*
Toro-Roman et al. (2005) Structural Analysis and Solution Studies of the Activated Regulatory Domain of the Response Regulator ArcA: A Symmetric Dimer Mediated by the alpha4-beta5-alpha5 Face. Journal of Molecular Biology, 349:11-26 (Year: 2005).*

U00096.2 (*Escherichia coli* str. K-12subtr. MG1655, complete genome, NCBI Reference sequence, priority to Sep. 1, 2011, 5 pages) (Year: 2011).*
Schneider, Thomas D. "Sequence walkers: a graphical method to display how binding proteins interact with DNA or RNA sequences." Nucleic acids research 25.21 (1997): 4408-4415.
Schumacher, Maria A., et al. "Structural basis for cooperative DNA binding by two dimers of the multidrug-binding protein QacR." The EMBO journal 21.5 (2002): 1210-1218.
Smith, Jenny G., et al. "A search for amino acid substitutions that universally activate response regulators." Molecular microbiology 51.3 (2004): 887-901.
Toro-Roman, Alejandro, Timothy R. Mack, and Ann M. Stock. "Structural analysis and solution studies of the activated regulatory domain of the response regulator ArcA: a symmetric dimer mediated by the α4-β5-α5 face." Journal of molecular biology 349.1 (2005): 11-26.
Wang, Xiaohu, et al. "A high-throughput percentage-of-binding strategy to measure binding energies in DNA-protein interactions: application to genome-scale site discovery." Nucleic acids research 36.15 (2008): 4863-4871.
Wu, Carl. "Heat shock transcription factors: structure and regulation." Annual review of cell and developmental biology 11.1 (1995): 441-469.
Yoshida, Takeshi, et al. "Transcription regulation of ompF and ompC by a single transcription factor, OmpR." Journal of Biological Chemistry 281.25 (2006): 17114-17123.
Subashchandrabose, Sargurunathan, et al. "Genome-wide detection of fitness genes in uropathogenic *Escherichia coli* during systemic infection." (2013): e1003788.
Thorsness, et al., "Inactivation of Isocitrate Dehydrogenase by Phosphorylation is Mediated by the Negative Charge of the Phosphate" J. Biol. Chem., 262, 22, p. 10422-10425, 1987.
Park, Dan M., and Patricia J. Kiley. "The Influence of Repressor DNA Binding Site Architecture on Transcriptional Control." mBio 5.5 (2014): e01684-14. (Inventors' published manuscript).
Ackers, Gary K., Madeline A. Shea, and Francine R. Smith. "Free energy coupling within macromolecules: the chemical work of ligand binding at the individual sites in co-operative systems." Journal of molecular biology 170.1 (1983): 223-242.
Barbieri, Christopher M., Ti Wu, and Ann M. Stock. "Comprehensive analysis of OmpR phosphorylation, dimerization, and DNA binding supports a canonical model for activation." Journal of molecular biology 425.10 (2013): 1612-1626.
Blanco, Alexandre G., et al. "Tandem DNA recognition by PhoB, a two-component signal transduction transcriptional activator." Structure 10.5 (2002): 701-713.

(Continued)

*Primary Examiner* — Neil P Hammell
(74) *Attorney, Agent, or Firm* — Daniel A. Blasiole; DeWitt LLP

(57) ABSTRACT

The invention provided herein relates to sequence determinants that elicit certain levels of gene expression and methods for obtaining engineered ligand-responsive gene switches comprising these sequence determinants. More particularly, the invention provided herein relates to molecular building blocks (i.e., discrete nucleotide sequences), synthetic ligand-responsive gene switches comprising an assembly of these molecular building blocks, and methods of using synthetic ligand-responsive gene switches as customizable and controllable expression systems and sensors.

21 Claims, 10 Drawing Sheets

Specification includes a Sequence Listing.

(56) References Cited

OTHER PUBLICATIONS

Butala, Matej, Darja Žgur-Bertok, and Steve Busby. "The bacterial LexA transcriptional repressor." Cellular and Molecular Life Sciences 66.1 (2009): 82-93.
Chao, Garlo, et al. "Aerobic regulation of isocitrate dehydrogenase gene (icd) expression in Escherichia coli by the arcA and fnr gene products." Journal of bacteriology 179.13 (1997): 4299-4304.
Chen, Zehua, et al. "Discovery of Fur binding site clusters in Escherichia coli by information theory models." Nucleic acids research 35.20 (2007): 6762-6777.
Cho, Byung-Kwan, Eric M. Knight, and Bernhard Ø. Palsson. "Transcriptional regulation of the fad regulon genes of Escherichia coli by ArcA." Microbiology 152.8 (2006): 2207-2219.
Cox, Robert Sidney, Michael G. Surette, and Michael B. Elowitz. "Programming gene expression with combinatorial promoters." Molecular systems biology 3.1 (2007).
Cunningham, Louise, et al. "Co-regulation of lipoamide dehydrogenase and 2-oxoglutarate dehydrogenase synthesis in Escherichia coli: characterisation of an ArcA binding site in the lpd promoter." FEMS microbiology letters 169.2 (1998): 403-408.
Datsenko, Kirill A., and Barry L. Wanner. "One-step inactivation of chromosomal genes in Escherichia coli K-12 using PCR products." Proceedings of the National Academy of Sciences 97.12 (2000): 6640-6645.
Drapal, Nikola, and Gary Sawers. "Purification of ArcA and analysis of is specific interaction with the pfl promoter-regulatory region." Molecular microbiology 16.3 (1995): 597-607.
Drew, Horace R., and Andrew A. Travers. "DNA structural variations in the E. coli tyrT promoter." Cell 37.2 (1984): 491-502.
Elledge, S. J., and R. W. Davis. "Position and density effects on repression by stationary and mobile DNA-binding proteins." Genes & development 3.2 (1989): 185-197.
Gao, Rong, Timothy R. Mack, and Ann M. Stock. "Bacterial response regulators: versatile regulatory strategies from common domains." Trends in biochemical sciences 32.5 (2007): 225-234.
Gerasimova, A. V., et al. "ArcA regulator of gamma-proteobacteria: identification of the binding signal and description of the regulon." Biophysics 48.1 (2003): 21-25.
Griffith, Kevin L., and Alan D. Grossman. "A degenerate tripartite DNA-binding site required for activation of ComA-dependent quorum response gene expression in Bacillus subtilis." Journal of molecular biology 381.2 (2008): 261-275.
Haugen, Shanil P., Wilma Ross, and Richard L. Gourse. "Advances in bacterial promoter recognition and its control by factors that do not bind DNA." Nature Reviews Microbiology 6.7 (2008): 507-519.
Jeon, Yesu, et al. "Multimerization of phosphorylated and non-phosphorylated ArcA is necessary for the response regulator function of the Arc two-component signal transduction system." Journal of Biological Chemistry 276.44 (2001): 40873-40879.
Kang, Yisheng, et al. "Genome-wide expression analysis indicates that FNR of Escherichia coli K-12 regulates a large number of genes of unknown function." Journal of bacteriology 187.3 (2005): 1135-1160.
Kasahara, M. E. G. U. M. I., et al. "Dual regulation of the ugp operon by phosphate and carbon starvation at two interspaced promoters." Journal of bacteriology 173.2 (1991): 549-558.
Keseler, Ingrid M., et al. "EcoCyc: a comprehensive database of Escherichia coli biology." Nucleic acids research 39.suppl 1 (2011): D583-D590.
Khalil, Ahmad S., and James J. Collins. "Synthetic biology: applications come of age." Nature Reviews Genetics 11.5 (2010): 367-379.
Kim, Soo-Ki, et al. "Dual Transcriptional Regulation of theEscherichia coli Phosphate-Starvation-InduciblepsiE Gene of the Phosphate Regulon by PhoB and the Cyclic AMP (cAMP)-cAMP Receptor Protein Complex." Journal of bacteriology 182.19 (2000): 5596-5599.
Ku, H. H. "Notes on the use of propagation of error formulas." Journal of Research of the National Bureau of Standards 70.4 (1966).
Lanzer, Michael, and Hermann Bujard. "Promoters largely determine the efficiency of repressor action." Proceedings of the National Academy of Sciences 85.23 (1988): 8973-8977.
Liu, Xueqiao, and Peter De Wulf. "Probing the ArcA-P modulon of Escherichia coli by whole genome transcriptional analysis and sequence recognition profiling." Journal of Biological Chemistry 279.13 (2004): 12588-12597.
Lynch, A. Simon, and E. C. Lin. "Transcriptional control mediated by the ArcA two-component response regulator protein of Escherichia coli: characterization of DNA binding at target promoters." Journal of bacteriology 178.21 (1996): 6238-6249.
Mack, Timothy R., Rong Gao, and Ann M. Stock. "Probing the roles of the two different dimers mediated by the receiver domain of the response regulator PhoB." Journal of molecular biology 389.2 (2009): 349-364.
Makino, Kozo, et al. "DNA binding of PhoB and its interaction with RNA polymerase." Journal of molecular biology 259.1 (1996): 15-26.
Makino, Kozo, et al. "Nucleotide sequence of the phoB gene, the positive regulatory gene for the phosphate regulon of Escherichia coli K-12." Journal of molecular biology 190.1 (1986): 37-44.
Malpica, Roxana, et al. "Identification of a quinone-sensitive redox switch in the ArcB sensor kinase." Proceedings of the National Academy of Sciences of the United States of America 101.36 (2004): 13318-13323.
Malpica, Roxana, et al. "Signaling by the arc two-component system provides a link between the redox state of the quinone pool and gene expression." Antioxidants & redox signaling 8.5-6 (2006): 781-795.
Maxam, Allan M., and Walter Gilbert. "[57] Sequencing end-labeled DNA with base-specific chemical cleavages." Methods in enzymology 65 (1980): 499-560.
McGuire, Abigail M., et al. "A weight matrix for binding recognition by the redox-response regulator ArcA-P of Escherichia coli." Molecular microbiology 32.1 (1999): 219-221.
Miller, JH. 1972. Experiments in molecular genetics. Cold Spring Harbor Laboratory, Cold Spring Harbor, NY. (Cover and Table of Contents only).
Narayanan, Anoop, et al. "An asymmetric heterodomain interface stabilizes a response regulator-DNA complex." Nature communications 5 (2014).
Neidhardt, Frederick C., Philip L. Bloch, and David F. Smith. "Culture medium for enterobacteria." Journal of bacteriology 119.3 (1974): 736-747.
Nesbit, A. D., et al. "Sequence-specific binding to a subset of IscR-regulated promoters does not require IscR Fe—S cluster ligation." Journal of molecular biology 387.1 (2009): 28-41.
Nesbit, A. D., et al. "ArcA and AppY antagonize IscR repression of hydrogenase-1 expression under anaerobic conditions, revealing a novel mode of O2 regulation of gene expression in Escherichia coli." Journal of bacteriology 194.24 (2012): 6892-6899.
Park, Dan M., et al. "The bacterial response regulator ArcA uses a diverse binding site architecture to regulate carbon oxidation globally." PLoS genetics 9.10 (2013): e1003839.
Pellicer, Maria Teresa, et al. "Cross-induction of glc and ace Operons ofEscherichia coli Attributable to Pathway Intersection Characterization of the glc Promoter." Journal of Biological Chemistry 274.3 (1999): 1745-1752.
Pellicer, M. Teresa, et al. "A mutational study of the ArcA-P binding sequences in the aldA promoter of Escherichia coli." Molecular and General Genetics MGG 261.1 (1999): 170-176.
Prost, Jean-Franois, et al. "Cra-Dependent Transcriptional Activation of the icd Gene of Escherichia coli." Journal of bacteriology 181.3 (1999): 893-898.
Rampersaud, Arfaan, Susan L. Harlocker, and Masayori Inouye. "The OmpR protein of Escherichia coli binds to sites in the ompF promoter region in a hierarchical manner determined by its degree of phosphorylation." Journal of Biological Chemistry 269.17 (1994): 12559-12566.

(56) References Cited

OTHER PUBLICATIONS

Ritzefeld, Markus, et al. "Cooperative Binding of PhoBDBD to Its Cognate DNA Sequence—A Combined Application of Single-Molecule and Ensemble Methods." Biochemistry 52.46 (2013): 8177-8186.
Rolfe, Matthew D., et al. "Transcript profiling and inference of *Escherichia coli* K-12 ArcA activity across the range of physiologically relevant oxygen concentrations." Journal of Biological Chemistry 286.12 (2011): 10147-10154.
Salmon, Kirsty A., et al. "Global Gene Expression Profiling in *Escherichia coli* K12 effects of oxygen availability and ArcA." Journal of Biological Chemistry 280.15 (2005): 15084-15096.
Schlax, Paula J., Michael W. Capp, and Thomas M. Record Jr. "Inhibition of Transcription Initiation bulacRepressor." Journal of molecular biology 245.4 (1995): 331-350.
Schneider, Thomas D. "Information content of individual genetic sequences." Journal of theoretical biology 189.4 (1997): 427-441.

\* cited by examiner

A.

B.

SEQUENCE LISTING

<160> NUMBER OF SEQ ID NOS: 38

<210> SEQ ID NO 1
<211> LENGTH: 16
<212> TYPE: DNA
<213> ORGANISM: Escherichia coli

<400> SEQUENCE: 1
tgttaatgat ttgtaa                                               16

<210> SEQ ID NO 2
<211> LENGTH: 5
<212> TYPE: DNA
<213> ORGANISM: Escherichia coli

<400> SEQUENCE: 2 tgtta                                                            5

<210> SEQ ID NO 3
<211> LENGTH: 26
<212> TYPE: DNA
<213> ORGANISM: Escherichia coli

<400> SEQUENCE: 3
tgttaatgat ttgtaattgg cttgtc                                    26

<210> SEQ ID NO 4
<211> LENGTH: 5
<212> TYPE: DNA
<213> ORGANISM: Escherichia coli

<400> SEQUENCE: 4 tcata                                                            5

<210> SEQ ID NO 5
<211> LENGTH: 26
<212> TYPE: DNA
<213> ORGANISM: Escherichia coli

<400> SEQUENCE: 5
tcataatgat ttgtaattgg cttgtc                                    26

<210> SEQ ID NO 6
<211> LENGTH: 26
<212> TYPE: DNA
<213> ORGANISM: Escherichia coli

<400> SEQUENCE: 6
tgttaatgat ttcaaattgg cttgtc                                    26

<210> SEQ ID NO 7
<211> LENGTH: 26
<212> TYPE: DNA
<213> ORGANISM: Escherichia coli

<400> SEQUENCE: 7
tgttaatgat ttgtaattgg cttcac                                    26

<210> SEQ ID NO 8
<211> LENGTH: 26
<212> TYPE: DNA
<213> ORGANISM: Escherichia coli

<400> SEQUENCE: 8

```
tcataatgat ttcaaattgg cttgtc                                        26
```

<210> SEQ ID NO 9
<211> LENGTH: 26
<212> TYPE: DNA
<213> ORGANISM: Escherichia coli

<400> SEQUENCE: 9

```
tgtcaatgat ttgtaattgg cttgtc                                        26
```

<210> SEQ ID NO 10
<211> LENGTH: 26
<212> TYPE: DNA
<213> ORGANISM: Escherichia coli

<400> SEQUENCE: 10

```
tgttaatgat ttgttattgg cttgtc                                        26
```

<210> SEQ ID NO 11
<211> LENGTH: 26
<212> TYPE: DNA
<213> ORGANISM: Escherichia coli

<400> SEQUENCE: 11

```
tgttaatgat ttgtcattgg cttgtc                                        26
```

<210> SEQ ID NO 12
<211> LENGTH: 26
<212> TYPE: DNA
<213> ORGANISM: Escherichia coli

<400> SEQUENCE: 12

```
tgttaatgat ttgtcattgg cttcac                                        26
```

<210> SEQ ID NO 13
<211> LENGTH: 26
<212> TYPE: DNA
<213> ORGANISM: Escherichia coli

<400> SEQUENCE: 13

```
tgtcaatgat ttgtcattgg cttgtc                                        26
```

<210> SEQ ID NO 14
<211> LENGTH: 26
<212> TYPE: DNA
<213> ORGANISM: Escherichia coli

<400> SEQUENCE: 14

```
tgttaatgat ttgtaattgg cttgtt                                        26
```

<210> SEQ ID NO 15
<211> LENGTH: 26
<212> TYPE: DNA
<213> ORGANISM: Escherichia coli

<400> SEQUENCE: 15

```
tgttaatgat ttgttattgg cttcac                                        26
```

<210> SEQ ID NO 16
<211> LENGTH: 26
<212> TYPE: DNA
<213> ORGANISM: Escherichia coli

<400> SEQUENCE: 16
tgttaatgat tgttattgg cttgtt								26

<210> SEQ ID NO 17
<211> LENGTH: 54
<212> TYPE: DNA
<213> ORGANISM: Escherichia coli

<400> SEQUENCE: 17
agagcaattt tttgttaatg atttgtaatt ggcttgtcaa tactaccta ttgt			54

<210> SEQ ID NO 18
<211> LENGTH: 54
<212> TYPE: DNA
<213> ORGANISM: Escherichia coli

<400> SEQUENCE: 18
agagcaattt tttcataatg atttgtaatt ggcttgtcaa tactaccta ttgt			54

<210> SEQ ID NO 19
<211> LENGTH: 54
<212> TYPE: DNA
<213> ORGANISM: Escherichia coli

<400> SEQUENCE: 19
agagcaattt tttgttaatg atttcaaatt ggcttgtcaa tactaccta ttgt			54

<210> SEQ ID NO 20
<211> LENGTH: 54
<212> TYPE: DNA
<213> ORGANISM: Escherichia coli

<400> SEQUENCE: 20
agagcaattt tttgttaatg atttgtaatt ggcttcacaa tactaccta ttgt			54

<210> SEQ ID NO 21
<211> LENGTH: 54
<212> TYPE: DNA
<213> ORGANISM: Escherichia coli

<400> SEQUENCE: 21
agagcaattt tttcataatg atttcaaatt ggcttgtcaa tactaccta ttgt			54

<210> SEQ ID NO 22
<211> LENGTH: 54
<212> TYPE: DNA
<213> ORGANISM: Escherichia coli

<400> SEQUENCE: 22
agagcaattt tttgttaatg atttgtaatt ggcttgtcaa tactatgtta ttgt			54

<210> SEQ ID NO 23
<211> LENGTH: 54
<212> TYPE: DNA
<213> ORGANISM: Escherichia coli

<400> SEQUENCE: 23
atgttaattt tttgttaatg atttgtaatt ggcttgtcaa tactaccta ttgt			54

<210> SEQ ID NO 24
<211> LENGTH: 54
<212> TYPE: DNA
<213> ORGANISM: Escherichia coli -continued

<400> SEQUENCE: 24
atgttaattt tttgttaatg atttcaaatt ggcttgtcaa tactaccta ttgt        54

<210> SEQ ID NO 25
<211> LENGTH: 54
<212> TYPE: DNA
<213> ORGANISM: Escherichia coli

<400> SEQUENCE: 25
agagcaattt tttgtcaatg atttgtaatt ggcttgtcaa tactaccta ttgt        54

<210> SEQ ID NO 26
<211> LENGTH: 54
<212> TYPE: DNA
<213> ORGANISM: Escherichia coli

<400> SEQUENCE: 26
agagcaattt tttgttaatg atttgttatt ggcttgtcaa tactaccta ttgt        54

<210> SEQ ID NO 27
<211> LENGTH: 54
<212> TYPE: DNA
<213> ORGANISM: Escherichia coli

<400> SEQUENCE: 27
agagcaattt tttgttaatg atttgtcatt ggcttgtcaa tactaccta ttgt        54

<210> SEQ ID NO 28
<211> LENGTH: 54
<212> TYPE: DNA
<213> ORGANISM: Escherichia coli

<400> SEQUENCE: 28
agagcaattt tttgttaatg atttgtcatt ggcttcacaa tactaccta ttgt        54

<210> SEQ ID NO 29
<211> LENGTH: 54
<212> TYPE: DNA
<213> ORGANISM: Escherichia coli

<400> SEQUENCE: 29
agagcaattt tttgtcaatg atttgtcatt ggcttgtcaa tactaccta ttgt        54

<210> SEQ ID NO 30
<211> LENGTH: 54
<212> TYPE: DNA
<213> ORGANISM: Escherichia coli

<400> SEQUENCE: 30
agagcaattt tttgttaatg atttgtaatt ggcttgttaa tactaccta ttgt        54

<210> SEQ ID NO 31
<211> LENGTH: 54
<212> TYPE: DNA
<213> ORGANISM: Escherichia coli

<400> SEQUENCE: 31
agagcaattt tttgttaatg atttgttatt ggcttcacaa tactaccta ttgt        54

<210> SEQ ID NO 32
<211> LENGTH: 54
<212> TYPE: DNA

```
<213> ORGANISM: Escherichia coli

<400> SEQUENCE: 32
agagcaattt tttgttaatg atttgttatt ggcttgttaa tactaccta ttgt          54

<210> SEQ ID NO 33
<211> LENGTH: 35
<212> TYPE: DNA
<213> ORGANISM: Artificial Sequence
<220> FEATURE:
<223> OTHER INFORMATION: Oligonucleotide primer -- upstream of ArcA

<400> SEQUENCE: 33
ggtagcaaac atgcagaccc cgcacattct tatcg                              35

<210> SEQ ID NO 34
<211> LENGTH: 54
<212> TYPE: DNA
<213> ORGANISM: Artificial Sequence
<220> FEATURE:
<223> OTHER INFORMATION: Oligonucleotide primer -- downstream of ArcA

<400> SEQUENCE: 34
gcgccgtttt ttttgacggt ggtaaagccg attagtgtag gctggagctg cttc         54

<210> SEQ ID NO 35
<211> LENGTH: 20
<212> TYPE: DNA
<213> ORGANISM: Artificial Sequence
<220> FEATURE:
<223> OTHER INFORMATION: minimal ArcA binding site

<400> SEQUENCE: 35
atgttaaaaa atgttaaaaa                                               20

<210> SEQ ID NO 36
<211> LENGTH: 5
<212> TYPE: DNA
<213> ORGANISM: Escherichia coli

<400> SEQUENCE: 36 tcaca                                                               5

<210> SEQ ID NO 37
<211> LENGTH: 5
<212> TYPE: DNA
<213> ORGANISM: Escherichia coli

<400> SEQUENCE: 37 tgtaa                                                               5

<210> SEQ ID NO 38
<211> LENGTH: 5
<212> TYPE: DNA
<213> ORGANISM: Escherichia coli

<400> SEQUENCE: 38 tcaaa                                                               5
```

OXYGEN-RESPONSIVE BACTERIAL GENE SWITCH

CROSS-REFERENCE TO RELATED APPLICATIONS

This application is a continuation of U.S. patent application Ser. No. 14/597,466, filed Jan. 15, 2015, which claims the benefit of U.S. Provisional Patent Application No. 61/928,292, filed Jan. 16, 2014; each of which is incorporated herein by reference as if set forth in its entirety.

STATEMENT REGARDING FEDERALLY FUNDED RESEARCH

This invention was made with government support under GM045844 awarded by the National Institutes of Health and DE-FC02-07ER64494 and DE-FG02-04ER25627 awarded by the US Department of Energy. The government has certain rights in the invention.

BACKGROUND

In *Escherichia coli*, the ArcA/B two component system, comprised of the membrane bound sensor kinase, ArcB, and the response regulator, ArcA, couples changes in the respiratory state of cells to a global transcriptional response. Under aerobic conditions, ArcB kinase activity is silenced, which maintains ArcA largely in an inactive, unphosphorylated state. As $O_2$ levels decrease, the proportion of phosphorylated ArcA (ArcA-P) increases accordingly, with maximal phosphorylation occurring under anaerobic conditions.

Under anaerobic conditions and upon phosphorylation, ArcA-P binds extensively to ArcA binding sites across the genome, directly repressing operons that encode enzymes of the TCA cycle (gltA, icdA, sdhCDAB-sucABCD, mdh, lpdA), and for the β-oxidation of fatty acids (fadH, fadBA, fadL, fadE, fadD, fadIJ), lactaldehyde (aldA)/lactate oxidation (lldPRD), and glycolate/glyoxylate oxidation (glcC, glcDEFGBA).

Under certain conditions, ArcA-P activates the expression of operons encoding three enzymes important for adapting to microaerobic or anaerobic environments: (1) cytochrome bd oxidase (cydAB) (Lynch et al., *J Bacteriol.* 178:6238-6249 (1996)); (2) pyruvate formate lyase (focA-pflB) (Drapal et al., *Mol. Microbiol.* 16:597-607 (1995)); and (3) hydrogenase 1 (hya) (Nesbit et al., *J Bacteriol.* 194:6892-6899 (2012)). Recent ChIP-seq and Gene expression profiling analyses indicate that the "ArcA regulon" is more extensive than originally expected, and includes comprehensive transcriptional repression of genes encoding proteins associated with oxidation of non-fermentable carbon sources.

SUMMARY

In one aspect, the present invention provides an isolated polynucleotide comprising a nucleic acid sequence selected from the group consisting of SEQ ID NOs:1-32. The present invention further provides a vector comprising a polynucleotide and a vector not natively linked to the polynucleotide, the polynucleotide comprising a nucleic acid sequence selected from the group consisting of SEQ ID NOs:1-32. The polynucleotide can be operably linked to a promoter.

In another aspect, the present invention provides a bacterial host cell comprising a vector comprising a polynucleotide operably linked to a promoter. The bacterial host cell can be *E. coli*.

In a further aspect, the present invention provides a gene switch. The gene switch can comprise one or more nucleic acid sequences having the sequence of a binding site of a transcriptional activator or transcriptional repressor. The gene switch can be configured to positively or negatively modify a gene expression level of a target nucleic acid sequence operably linked to the gene switch. The one or more nucleic acid sequences can be selected from the group consisting of SEQ ID NOs:1-32. The gene switch can comprise 1, 2, 3, 4, or 5 repeats of a nucleic acid sequence selected from the group consisting of SEQ ID NOs:1-32.

In another aspect, the present invention provides a method for modifying a level of gene expression. The method can comprise introducing into a host cell an expression vector comprising a gene switch. The gene switch can comprise one or more nucleic acid sequences having the sequence of a binding site of a transcriptional activator or transcriptional repressor operably linked to a promoter and is configured to positively or negatively modify a gene expression level of a target nucleic acid sequence operably linked to the gene switch when the host cell is subjected to a change in oxygen concentration. The gene expression level can be modified under anaerobic conditions. The gene switch can comprise one or more nucleic acid sequences selected from the group consisting of SEQ ID NOs:1-32. The gene switch can comprise 1, 2, 3, 4, or 5 repeats of a nucleic acid sequence selected from the group consisting of SEQ ID NOs:1-32. Expression of the target nucleic acid sequence can be increased relative to a host cell lacking the expression vector. Expression of the target nucleic acid sequence can be decreased relative to a bacterial host cell lacking the expression vector. The bacterial host cell can be *E. coli*.

In yet another aspect, the present invention provides a method of modifying a level of gene expression. The method can comprise introducing into a bacterial host cell an expression vector comprising a gene switch. The gene switch can comprise one or more nucleic acid sequences having the sequence of a PhoB binding site operably linked to a promoter. The gene switch can be configured to positively or negatively modify a gene expression level of a target nucleic acid sequence operably linked to the gene switch when the bacterial host cell is subjected to a change in inorganic phosphate (Pi) levels. Expression of the target nucleic acid sequence can be increased relative to a bacterial host cell lacking the expression vector. Expression of the target nucleic acid sequence can be decreased relative to a bacterial host cell lacking the expression vector. The host cell can be *E. coli*.

These and other features, aspects, and advantages described herein will become better understood from the description that follows. In the description, reference is made to the accompanying drawings, which form a part hereof and in which there is shown by way of illustration, not limitation, embodiments of the invention. The description of preferred embodiments is not intended to limit the invention to cover all modifications, equivalents and alternatives. Reference should therefore be made to the claims recited herein for interpreting the scope of the invention.

BRIEF DESCRIPTION OF THE DRAWINGS

The present invention will be better understood and features, aspects and advantages other than those set forth above will become apparent when consideration is given to the following detailed description thereof. The detailed description makes reference to the following drawings, where.

DETAILED DESCRIPTION

Figure 1:
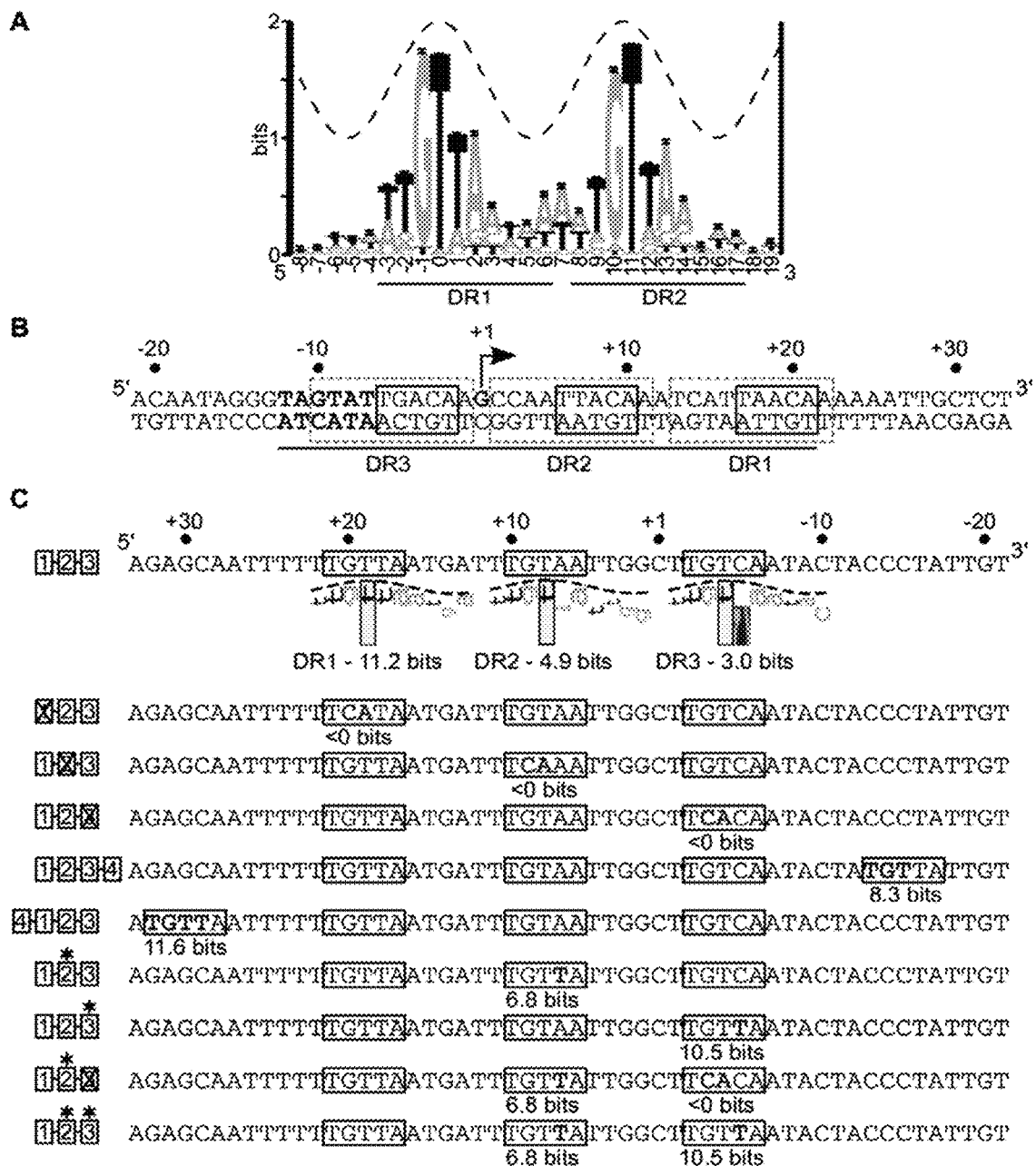
FIG. 1 presents the regulatory region of the wild-type icdA ($P_1$) promoter from E. coli containing all three DR elements. (A) Sequence logo for the minimal ArcA binding site consisting of two 10-basepair (bp) direct repeat elements (5'-ATGTTAAAAA-1-ATGTTAAAAA-3') (SEQ ID NO:35). The total sequence conservation is 15.6±0.07 bits in the range from positions 3 to +14. The crest of the sine wave represents the major groove of B-form DNA. (B) Regulatory region of the icdA $P_1$ promoter from E. coli (SEQ ID NO:17). The arrow indicates the position of the previously mapped transcription start site (5), with the $\sigma^{70}$-RNAP −10 promoter element in bold. Each of three 10-bp DR elements is indicated by dashed-line gray boxes, with the most conserved 5-bp 5'-TGTTA-3' (SEQ ID NO:2) region within each DR element indicated with a solid-line black box. The ArcA-P footprint region is indicated underneath the sequence by the black line. (C) Noncoding strand of the icdA-lacZ promoter, depicting the ArcA binding site mutations used in this study (SEQ ID NOS:17-20, 22, 23, 26, 30, 31, and 32). The degree of match of each DR element to the 10-bp ArcA DR element PWM is indicated in bits and visualized using sequence walkers (Schneider, *Nucleic Acids Res.* 25:4408-15 (1997)). The purple box surrounding the C at position 6 indicates a contact that is more unfavorable than −4 bits and, thus, off the scale. The boxes to the left of the binding sites are the key used to indicate mutations in subsequent figures. Mutations away from the consensus in each DR element [5'-TGTTA-3' (SEQ ID NO:2) to 5'-TCATA-3' (SEQ ID NO: 4)] are indicated in red and labeled with a x in the cartoon, while mutations toward the consensus are indicated in blue and are labeled with an asterisk. The information content for all 10 bp of each mutated DR element is listed below the DR element.

All publications, patents, and patent applications mentioned in this specification are herein incorporated by reference in their entirety as if each individual publication, patent, and patent application was specifically and individually indicated to be incorporated by reference.

The ArcB/ArcA two-component signal transduction system of *Escherichia coli* regulates gene expression in response to the redox conditions of growth. ArcA's function as a dual transcriptional regulator for anoxic redox control is primarily to negatively regulate transcription under anaerobic conditions. Negative regulation under anaerobic conditions comprises repressing operons involved in respiratory metabolism, but also activating some operons that encode proteins involved in fermentative metabolism. The present invention is based, at least in part, on Applicants' discovery that ArcA represses expression of nearly all carbon utilization pathways for which recycling of redox carriers is coupled to respiration, and that complex structural and sequence determinants govern ArcA's regulatory mechanisms. ArcA binding sites within the promoter regions of these regulated operons almost exclusively overlap the $\sigma^{70}$-RNA polymerase ($\sigma^{70}$-RNAP) recognition elements and contain a variable number of direct repeat (DR) sequence elements. By binding and repressing ArcA DNA, these cis-regulatory elements play an important role in global reprogramming of metabolism. Accordingly, the invention provided herein relates to exploiting ArcA's regulatory mechanisms by identifying sequence determinants that elicit certain levels of gene expression and using these sequence determinants as tools to engineer ligand-responsive gene switches. More particularly, the invention provided herein relates to molecular building blocks (i.e., discrete nucleotide sequences), synthetic ligand-responsive gene switches comprising an assembly of these molecular building blocks, and methods of using synthetic ligand-responsive gene switches as customizable expression systems and sensors.

Compositions of the Invention

In a first aspect, the present invention provides isolated nucleic acids. An isolated nucleic acid of the invention can have a nucleotide sequence having the sequence of an ArcA sequence determinant. The putative consensus ArcA-P binding site in the *E. coli* icdA (isocitrate dehydrogenase A) promoter region is 5'-TGTTAATGATTTGTAA-3' (SEQ ID NO:1). In some cases, an isolated nucleic acid of the present invention comprises a portion of the consensus sequence such as, for example, 5'-TGTTA-3' (SEQ ID NO:2). In some cases, an isolated nucleic acid of the present invention comprises one or more nucleotide sequences selected from the sequences set forth in Table 1. In Table 1, mutations that decrease sequence identity with the ArcA consensus site from the icdA promoter (mutation away from consensus) are presented in bold, underlined font.

TABLE 1

ArcA Sequence Determinants

| Nucleotide Sequence (5'-3') | SEQ ID NO: |
|---|---|
| TGTTAATGATTTGTAA | 1 |
| TGTTA | 2 |
| TGTTAATGATTTGTAATTGGCTTGTC | 3 |
| TCATA | 4 |
| TCATAATGATTTGTAATTGGCTTGTC | 5 |
| TGTTAATGATTTCAAATTGGCTTGTC | 6 |
| TGTTAATGATTTGTAATTGGCTTCAC | 7 |
| TCATAATGATTTCAAATTGGCTTGTC | 8 |
| TGTCAATGATTTGTAATTGGCTTGTC | 9 |
| TGTTAATGATTTGTTATTGGCTTGTC | 10 |
| TGTTAATGATTTGTCATTGGCTTGTC | 11 |
| TGTTAATGATTTGTCATTGGCTTCAC | 12 |
| TGTCAATGATTTGTCATTGGCTTGTC | 13 |
| TGTTAATGATTTGTAATTGGCTTGTT | 14 |
| TGTTAATGATTTGTTATTGGCTTCAC | 15 |
| TGTTAATGATTTGTTATTGGCTTGTT | 16 |

In a second aspect, the present invention provides a gene switch. As used herein, the term "gene switch" refers to nucleotide sequences comprising binding sites for specific regulatory proteins (i.e., transcription factors) that operate as transcriptional repressors or transcriptional activators. In general, gene switches are located upstream of the regulated gene and within its promoter region. In some cases, multiple gene switches are associated with a gene.

In some cases, a single nucleotide sequence provided herein can be a synthetic gene switch. In exemplary embodiments, multiple (e.g., two or more) nucleotide sequences are assembled to form a synthetic gene switch. In some cases, a gene switch comprises one or more repeats of a portion of a minimal consensus sequence: 5'-TGTTA-3' (SEQ ID NO:2). In other cases, a gene switch comprises one or more repeats of a sequence set forth in Table 1 or Table 2. As in Table 1, Table 2 presents mutations towards the ArcA consensus site from the icdA promoter in bold font and presents mutations away from the ArcA consensus site in bold, underlined font.

TABLE 2

ArcA Binding Site Mutants at the icdA Promoter

| Name | SEQ ID NO: | Sequence |
|---|---|---|
| icdA WT (P1) | 17 | AGAGCAATTTTTGTTAATGATTTGTA ATTGGCTTGTCAATACTACCCTATTGT |
| DR1 GT->CA | 18 | AGAGCAATTTTTCATAATGATTTGTA ATTGGCTTGTCAATACTACCCTATTGT |
| DR2 GT->CA | 19 | AGAGCAATTTTTGTTAATGATTTCAA ATTGGCTTGTCAATACTACCCTATTGT |
| DR3 GT->CA | 20 | AGAGCAATTTTTGTTAATGATTTGTA ATTGGCTTCACAATACTACCCTATTGT |
| DR1 GT->CA, DR2 GT->CA | 21 | AGAGCAATTTTTCATAATGATTTCAA ATTGGCTTGTCAATACTACCCTATTGT |
| 3' DR4 | 22 | AGAGCAATTTTTGTTAATGATTTGTA ATTGGCTTGTCAATACTATGTTATTGT |
| 5' DR4 | 23 | ATGTTAATTTTTGTTAATGATTTGTA ATTGGCTTGTCAATACTACCCTATTGT |
| 5' DR4, DR2 GT->CA | 24 | ATGTTAATTTTTGTTAATGATTTCAA ATTGGCTTGTCAATACTACCCTATTGT |
| DR1 T->C | 25 | AGAGCAATTTTTGTCAATGATTTGTA ATTGGCTTGTCAATACTACCCTATTGT |
| DR2 A->T | 26 | AGAGCAATTTTTGTTAATGATTTGTT ATTGGCTTGTCAATACTACCCTATTGT |
| DR2 A->C | 27 | AGAGCAATTTTTGTTAATGATTTGTC ATTGGCTTGTCAATACTACCCTATTGT |
| DR2 A->C, DR3 GT->CA | 28 | AGAGCAATTTTTGTTAATGATTTGTC ATTGGCTTCACAATACTACCCTATTGT |
| DR1 T->C, DR2 A->C | 29 | AGAGCAATTTTTGTCAATGATTTGTC ATTGGCTTGTCAATACTACCCTATTGT |
| DR3 C->T | 30 | AGAGCAATTTTTGTTAATGATTTGTA ATTGGCTTGTTAATACTACCCTATTGT |

TABLE 2-continued

ArcA Binding Site Mutants at the icdA Promoter

| Name | SEQ ID NO: | Sequence |
|---|---|---|
| DR2 A->T, DR3 GT->CA | 31 | AGAGCAATTTTTGTTAATGATTTGTT ATTGGCTTCACAATACTACCCTATTGT |
| DR2 A->T, DR3 C->T | 32 | AGAGCAATTTTTGTTAATGATTTGTT ATTGGCTTGTTAATACTACCCTATTGT |

In general, a gene switch of the present invention can comprise a nucleotide sequence capable of positively or negatively modifying a gene expression level when placed upstream of a gene, open reading frame (ORF), or operon of interest. The level of gene expression elicited by a gene switch corresponds to the level of binding sensitivity and, thus, is nucleotide sequence dependent. As used herein, the term "operon" refers to cluster of coding sequences transcribed as a single mRNA molecule. An operon may additionally include transcriptional elements such as a promoter region and a transcription terminator region that regulate the expression of the genes encoding the proteins.

In some cases, a gene switch of the present invention is capable of providing an "ON/OFF switch" for tightly-regulated gene expression. In other cases, a gene switch is capable of affecting transcriptional regulation in a graded or linear manner. For example, transcriptional regulation for a gene of interest can vary over at least a 10- or 15-fold (e.g., at least 10-, 15-, 20-, 30-, 40-, 50-, or 60-fold) range in response to changes in oxygen and carbon availability or in response to cell membrane perturbations.

In some cases, a gene switch comprises one, two, three, four, or five repeats of a sequence described herein. In an exemplary embodiment, a gene switch comprises at least two sequences, where there is a 11-basepair (bp) center-to-center (ctc) spacing interval between consecutive promoter sequence repeats. In other words, a gene switch can comprise at least two consecutive promoter sequence repeats, where the center of a first promoter sequence is 11 bp away from the center of its adjacent promoter sequence. In other cases, a gene switch comprises at least two sequences, where there is a 22-bp ctc spacing interval between consecutive promoter sequence repeats. Such a gene switch is likely to be a weaker negative regulator (i.e., weaker repressor) of transcription than a gene switch having the same number of sequence repeats but comprising 11-bp ctc spacing between consecutive sequence repeats.

In some cases, a gene switch having high sensitivity to changes in ArcA-P levels can comprise three or four sequence repeats having an 11-bp spacing interval. For example, a gene switch having high sensitivity to changes in ArcA-P levels can comprise SEQ ID NO:23 (5' ATGTTAAT-TTTTTGTTAATGATTTGTAATTGGCTTGTCAATAC-TACCCTATTGT-3') with 11-bp ctc spacing.

A gene switch of the present invention can further comprise promoter elements capable of fine-tuning the expression of a gene, operon, or ORF of interest, in response to an endogenous inducer such as $O_2$. Levels of Arc-P can change in response to a change in an environmental condition such as, for example, an increase or decrease in $O_2$ concentration or an increased or decreased ratio of NADH to $NAD^+$.

In some cases, a gene switch of the present invention comprises at least a portion of a RNA polymerase (RNAP) binding site. For example, a gene switch sequence can at least partially overlap the "−35 region" and the "−10 region," which are nucleotide sequences associated with the recognition and binding of RNA polymerase. In some cases, a gene switch comprises at least a portion of a bacterial $\sigma^{70}$-RNAP binding site. A RNAP binding site, or portion thereof, can be upstream (5') or downstream (3') relative to a transcriptional start site.

The ArcA binding site can repress transcription when centered anywhere from −50 to +20 bp relative to a transcriptional start site. In some cases, transcription is repressed at least 2-fold. Transcription can be repressed to a degree anywhere between 2-fold and 100-fold repression (e.g., at least 2-fold, 4-fold, 6-fold, 8-fold, 10-fold, 12-fold, 14-fold, 16-fold, 18-fold, 20-fold, 40-fold, 60-fold, 80-fold, 100-fold repression).

In a further aspect, the present invention provides a synthetic sensor or "biosensor." Synthetic biosensors typically comprise modules for sensing and responding, to diverse, transient environmental signals. Both functions can be placed under synthetic control by directly engineering environment-responsive promoter sequences. A transcriptional sensor can comprise an environment-responsive promoter and a nucleotide sequence, transcription of which is activated in response to an environmental signal.

Methods of the Invention. In another aspect, the present invention provides methods for controlling transcription. In particular, methods of the present invention are useful for achieving ligand-responsive transcriptional control over a gene, operon, or ORF of interest. As used herein, the term "ligand-responsive" refers to phosphorylation of ArcA via activation of the kinase of ArcB by removal of $O_2$. Accordingly, a gene switch of the present invention can be used to regulate transcription in response to, for example, changes in oxygen and carbon availability, a cell membrane perturbation, changes in NADH/NAD$^+$ ratios, or changes in the oxidation-reduction state of a membrane quinone pool. Membrane perturbations leading to malfunction of the aerobic respiratory chain can be caused by, for example, the production or export of hydrophobic compounds, biofuel precursors, or recombinant proteins.

According to one method of the invention, an expression system comprising a gene switch is transformed into a suitable microorganism host (e.g., *E. coli*). As used herein, the term "expression system" refers to DNA sequences containing a desired coding sequence and control sequences in operable linkage, such that a host cell transformed with these sequences is capable of producing the encoded proteins. In order to effect transformation, an expression system may be included on a vector. In some cases, therefore, a gene switch is operably linked to a gene, operon, or ORF of interest and cloned into an appropriate vector. Any appropriate vector can be used with a nucleotide sequence of the present invention. Without limitation, appropriate vectors for methods of the invention include pBR322, pACYC184, and pSC101.

With respect to bacterial components useful for practicing the presently claimed methods, a standard approach is to drive the expression of pathway components with strong, exogenous promoters such as the PLtet, PLlac, and PBAD promoters from the tet, lac, and ara operons of *E. coli*, respectively. See Khalil and Collins, *Nat Rev Genet.* 11(5): 367-379 (2011).

Any appropriate methodology can be used to introduce an expression system into a host cell. For example, an expression system can be introduced into a host cell using a heat-shock transformation protocol. Without limitation, appropriate bacterial strains appropriate for methods of the invention described herein include the following *E. coli* strains: MG1655, BW25993, and DH5a.

In some cases, a method according to the present invention comprises repressing transcription to slow or halt production of a gene product. Any appropriate methodology can be used to detect and measure a change in, for example, levels of transcription of mRNA of the gene or operon of interest or levels of production of the gene product of interest. In some cases, changes in transcription or translation can be detected or measured using a reporter such as, for example, a fluorescent or bioluminescent reporter.

In another aspect, a method of the present invention can comprise introducing an expression system comprising a gene switch into a host cell, where the gene switch is sensitive to one or more particular environmental condition whereby a change in such an environmental condition is associated with a positive or negative change in expression of a gene operably linked to the gene switch. Without limitation, environmental conditions to which a gene switch can have sensitivity include changes in oxygen concentration (oxygen availability) and changes in NADH/NAD$^+$ ratios. Accordingly, a method of the present invention can comprise introducing into a host cell an expression system comprising a gene switch having sensitivity to oxygen availability and exposing the host cell to a positive or negative change in oxygen availability, thereby eliciting a change in gene expression. Preferably, the change in gene expression is detectable.

In another aspect, a method of the present invention can comprise introducing an expression system comprising a gene switch into a host cell, where the gene switch is sensitive to one or more particular environmental condition whereby a change in such an environmental condition is associated with a positive or negative change in expression of a gene operably linked to the gene switch and is further associated with altered bacterial growth. Without limitation, altered bacterial growth can include changes in replication rates (e.g., positive or negative changes in the number of doubling per hour), bacterial density, and metabolic activity (e.g., oxygen consumption, acid production). Accordingly, a method of the present invention can comprise introducing into a host cell an expression system comprising a gene switch having sensitivity to oxygen availability and exposing the host cell to a positive or negative change in oxygen availability, thereby eliciting a change in gene expression and further altering bacterial growth. Preferably, an alteration in bacterial growth is detectable.

Also encompassed by the present invention are methods of using a synthetic sensor or biosensor described herein for drug discovery or drug production. Generally, synthetic sensors are useful for systematically probing the function of individual components of an oxygen consumption pathway. For example, a synthetic biosensor can feature an ArcA-P gene biosensor featuring an ArcA-based transactivator of a reporter gene for use with a screen to identify ArcA inhibitors. If a cell-based assay is used to identify pathway components or targets, the assay intrinsically enriches for inhibitors that are membrane-permeable and non-toxic to cells.

The methods described herein can be used in connection with oxygen consumption pathways as well as other pathways that consume NADH (i.e., reducing intracellular NAD+ to NADH). Inducible promoter elements of the present invention can be used to tightly control expression of a gene or operon of interest in a system that is responsive to the intracellular ratio of NADH/NAD+. In such a system, the rate of oxygen consumption increases as the intracellular NADH/NAD+ ratio increases, whereas a decrease in the NADH/NAD+ ratio results in a decreased rate of oxygen consumption.

A method of the present invention can be based on a metabolic regulation pathway of any appropriate global bacterial regulator in order to exert transcriptional control for a gene of interest in the presence of a particular environmental stimulus (e.g., carbon flow, nutrient starvation, oxygen stress, nitrogen levels, phosphate levels, temperature, pH, osmotic strength). For example, a method can comprise altering transcription of a gene of interest using a phosphorylation-activated gene switch such as a transcriptional regulator from the OmpR (osmoregulatory protein)/PhoB (*E. coli* phosphate assimilation regulator) subfamily. As used herein, the term "transcriptional regulator" refers to a regulatory factor of two-component signal transduction systems. Genes whose expression is modulated in response to the external concentration of inorganic phosphate (Pi) are often regulated by the PhoB protein which binds to a conserved binding motif (an 18 nucleotide sequence known as a "Pho box" or PhoB binding motif) within their promoter regions. The PhoB transcriptional regulator, which is part of the PhoB-PhoR two-component signaling system, can sense a limitation of extracellular Pi to activate expression of a target gene. Direct repeat elements having 11-bp center-to-center spacing are found within PhoB regulated promoters. For example, the pstS promoter comprises two 7 nucleotide (nt) DRs of 5'-CTGTCAT-3' are separated by a conserved 4 nt spacer and are situated 10 basepairs upstream of the −10 region. See Makino et al., *J. Mol. Biol.* 190:37-44 (1986); Makino et al., *J. Mol. Biol.* 259(1):15-26 (1996). Because the Pho regulon operates similarly to the ArcA regulon in bacteria, the regulatory logic of the icdA promoter is expected to apply. Accordingly, a gene switch of the present invention can comprise nucleotide sequence from a PhoB regulated promoter. Without limitation, PhoB regulated promoters useful for the present invention include the following *E. coli* promoters: psiE (Kim et al., *J. Bacteriol.* 182:5596-5599 (2000)), ugpB (Kasahara et al., *J. Bacteriol.* 173:549-558 (1991)), and pstS (Makino et al., *J. Mol. Biol.* 259(1): 15-26 (1996)).

While the present invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents and alternatives falling within the spirit and scope of the invention as defined by the appended claims.

The invention will be more fully understood upon consideration of the following non-limiting Examples.

EXAMPLES

Example 1

Figure 2:
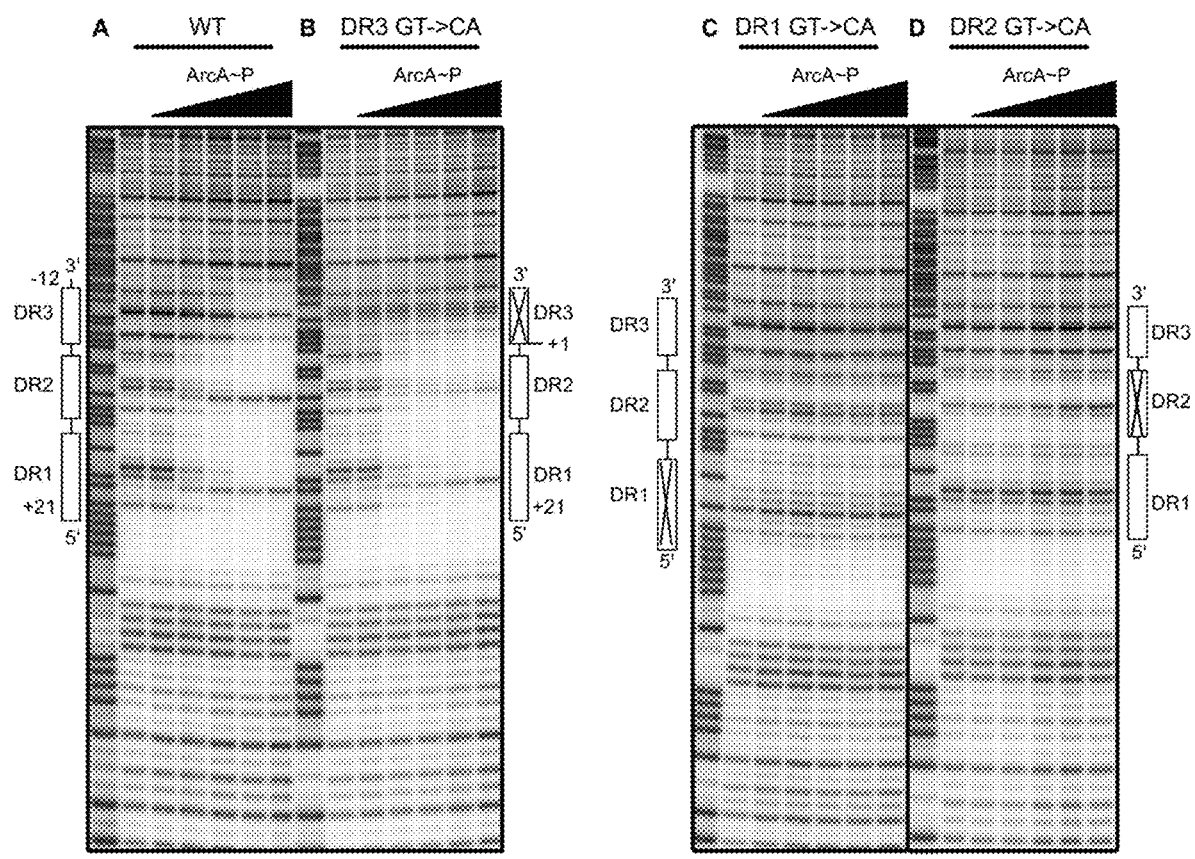
FIG. 2 presents DNase I footprinting of ArcA binding to the wt or mutated icdA promoter region. (A) wt ArcA binding site containing all three DR elements; (B) elimination of DR3 by a 5'-TGTCA-3' (SEQ ID NO: 39) to 5'-TCACA-3' (SEQ ID NO:36) mutation; (C) elimination of DR1 by a 5'-TGTTA-3' (SEQ ID NO:2) to 5'-TCATA-3' (SEQ ID NO:4) mutation; (D) elimination of DR2 by a 5'-TGTAA-3' (SEQ ID NO:37) to 5'-TCAAA-3' (SEQ ID NO:38) mutation. The regions protected by ArcA-P are indicated with vertical lines and are numbered to indicate the position relative to a previously determined transcription start site (Chao et al., *J. Bacterial.* 179:4299-4304 (1997)). The 10-bp DR elements are indicated by open boxes, with a x representing a DR element that has been eliminated through mutation (see FIG. 1C). Samples were electrophoresed with Maxam-Gilbert ladders (A+G) made using the same DNA (lane 1). ArcA-P protein concentrations are given from left to right in nM total ArcA-P protein as follows: 0, 50, 150, 300, 600, and 1,000 nM.

ArcA Binding Site Architecture at the icdA Promoter Broadens the Sensitivity of Repression to ArcA-P Levels Assays were developed to observe the effects of modulating ArcA binding site architectures on absolute anaerobic and aerobic expression and on sensitivity of ArcA repression to experimental conditions that alter ArcA-P levels. Such experimental conditions include changes in $O_2$ concentration and NADH/NAD$^+$ ratios. Assays were performed to test to role of each of three predicted 10-bp direct repeat (DR) elements (DR1-1-DR2-1-DR3) in ArcA DNA binding to $P_{1icdA}$. Specifically, DNase I footprinting was performed using ArcA-P and either the wild type (wt) icdA promoter fragment or those in which each DR element was individually disrupted through mutation of highly conserved GT to CA (5'-TGTTA-3' to 5'-TCATA-3') (SEQ ID NO:2; SEQ ID NO:4, respectively), reducing the information content of each DR element below the theoretical lowest limit of binding (0 bits) (FIG. 1C). As previously observed (Park et al., *PLoS One Genetics* 9:e1003839 (2013)), ArcA-P protected the three DR elements of the wt promoter region from −12 to +21 relative to the TSS (FIG. 2A). More ArcA-P (600 nM) was required to observe maximum occupancy of the lower-information-content site, DR3 (3.0 bits), than the higher-information-content sites, DR1(11.2 bits) and DR2 (4.9 bits) (300 nM). Disruption of either DR1 or DR2 eliminated ArcA-P protection of all three DR elements, even at the highest ArcA-P levels tested (FIGS. 2C-D). In contrast, when DR3 was mutated, ArcA-P binding to only DR3 was eliminated (FIG. 2B). Furthermore, the amount of ArcA-P required for maximal binding of either DR1 or DR2 was not affected by disruption of DR3, suggesting that ArcA binding to DR1 and DR2 is not enhanced by ArcA-P interactions with DR3 despite the dependence of DR3 binding on ArcA-P interactions with DR1 and DR2. Overall these results suggest that ArcA-P binding to DR1 and DR2 appears to be cooperative and independent of ArcA binding to DR3.

Figure 3:
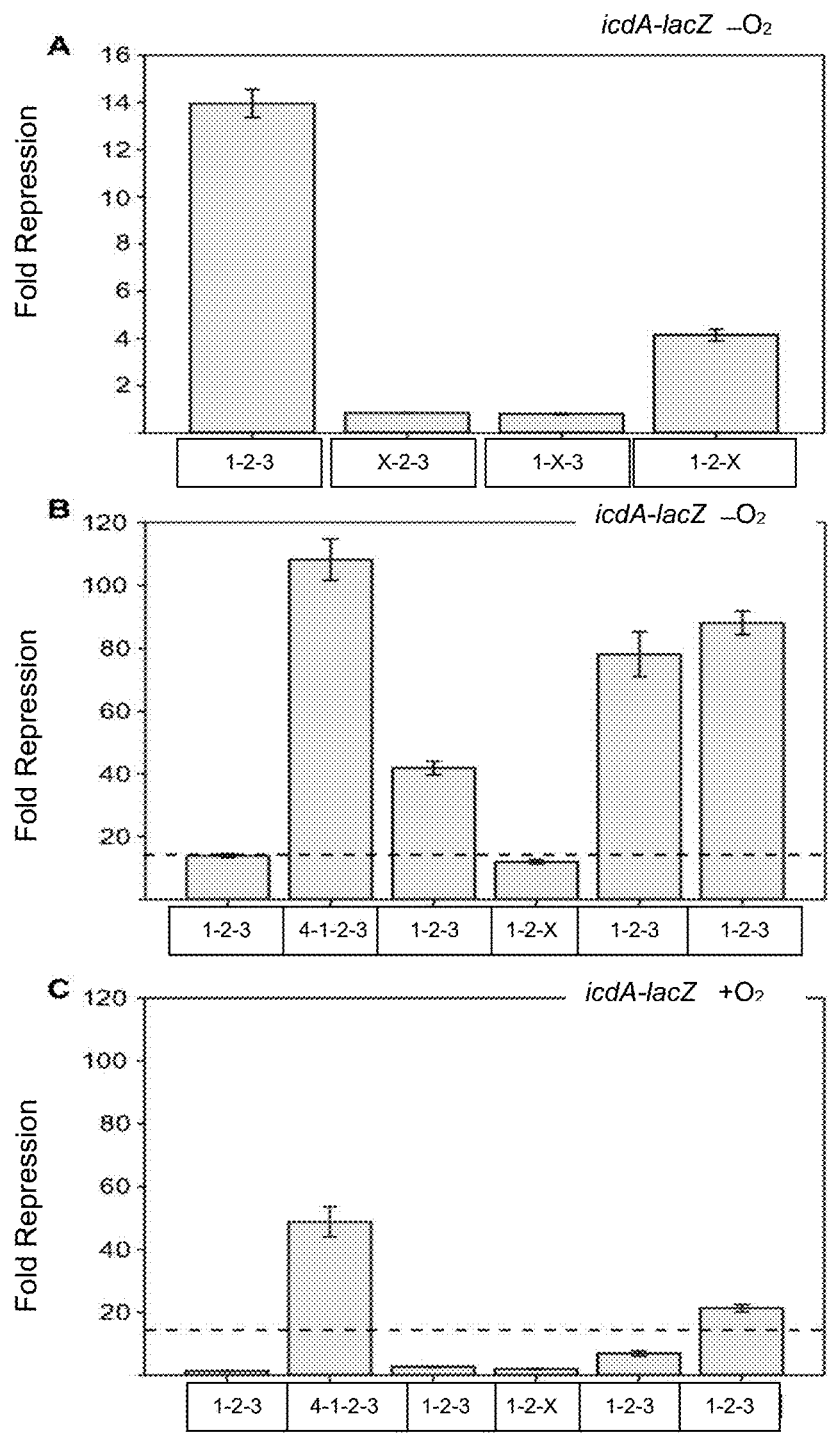
FIG. 3 demonstrates the effect of mutations on ArcA-dependent repression of the icdA promoter. Strains containing $P_{1icdA}$-lacZ were grown in minimal media with 0.2% glucose. Fold repression was calculated by dividing the β-galactosidase activity of a ΔarcA strain (e.g., 803 Miller units for wt $P_{1icdA}$ without $O_2$) by the activity of an arcA$^+$ strain (e.g., 57 Miller units for wt $P_{1icdA}$ without $O_2$). The 10-bp DRs are indicated by open boxes with an X representing a DR element for which the repressive activity has been eliminated by mutation, and asterisks denoting DRs that have been mutated towards consensus (see FIG. 1C). (A) Effects of mutations away from consensus within each DR element, assayed under anaerobic conditions (—$O_2$). (B) The effect of mutations towards consensus within each DR element, assayed under anaerobic conditions. The dotted line represents anaerobic ArcA-dependent repression of wt $P_{1icdA}$. (C) The effect of mutations towards consensus within each DR element, assayed under aerobic conditions. Error bars represent the standard errors of results of at least three independent replicates. $P_{1icdA}$ expression in the construct with a fourth DR element was about 18% higher in a ΔarcA background compared to the other strains tested (data not shown).

The mechanisms governing the occupancy of DR3 may be complex, since we found that an N-terminal His tag variant of ArcA-P also eliminated binding to DR3, but not DR1 and DR2 (data not shown), suggesting that protein-protein interactions may be important for stabilizing ArcA-P binding to DR3. We also found that disruption of DR3 weakened a hypersensitive band at position +8 within DR2 (FIGS. 3A-B). Because DNase I is sensitive to the minor groove width, this change in hypersensitivity may suggest that ArcA-P bends or kinks the DNA to a greater degree when bound to all three DR elements than when bound to just DR1 and DR2. Thus, an ArcA-P dimer bound to DR1 and DR2 may also stabilize the binding of ArcA-P to DR3 by bending the DNA.

How ArcA binding to each DR element contributes to icdA repression was determined by measuring β-galactosidase activity produced from $P_{1icdA}$-lacZ transcriptional fusions containing the GT-to-CA (5'-TGTTA-3' to 5'-TCATA-3') (SEQ ID NO:2; SEQ ID NO:4, respectively) mutations within each DR element under anaerobic conditions. Basal promoter activity was not altered by any binding site mutation, as all variants exhibited the same activity as the wt promoter in the absence of ArcA repression (data not shown). $P_{1icdA}$ was repressed 14-fold by ArcA (FIG. 3A). However, disruption of either DR1 or DR2 completely abolished ArcA-dependent repression (FIG. 3A), consistent with the loss of DNA binding to all three DRs observed by DNase I footprinting (FIGS. 2C-D). In contrast, disruption of DR3, which did not perturb ArcA binding to DR1 and DR2 (FIG. 2B), showed an ~3.5-fold loss in repression (FIG. 3A). This result suggests that in vivo occupancy of DR1 and DR2 is sufficient to direct a moderate amount of $P_{1icdA}$ repression but that additional occupancy of DR3 is required for maximal repression, perhaps because it overlaps the −10 promoter element.

Since DR2 and DR3 contain a lower information content than DR1, we tested whether mutations that improve the information content affect repression under anaerobic conditions. Mutation of DR2 toward the consensus (5'-TGTAA-3' to 5'-TGTTA-3') resulted in a 3-fold increase in anaerobic repression of $P_{1icdA}$ (FIG. 3B). This repression still depends on DR3 function, since the additional disruption of DR3 (5'-TGTCA-3' to 5'-TCACA-3') caused the same 3-fold reduction in repression as observed when DR3 was disrupted in an otherwise wt icdA sequence (FIGS. 3A-B). When just DR3 was mutated toward the consensus (5'-TGTCA-3' to 5'-TGTTA-3'), repression was increased 6-fold (FIG. 3B). Improving both DR2 and DR3 toward the consensus resulted in a level of repression similar to that observed with a consensus DR3 element alone, suggesting that maximal $P_{1icdA}$ repression by ArcA had been achieved (FIG. 3B). Assuming that these nucleotide changes simply improve DNA binding affinity, the enhanced anaerobic repression suggests that the three DRs of wt icdA are not completely occupied by ArcA under our standard anaerobic growth conditions.

Figure 4:
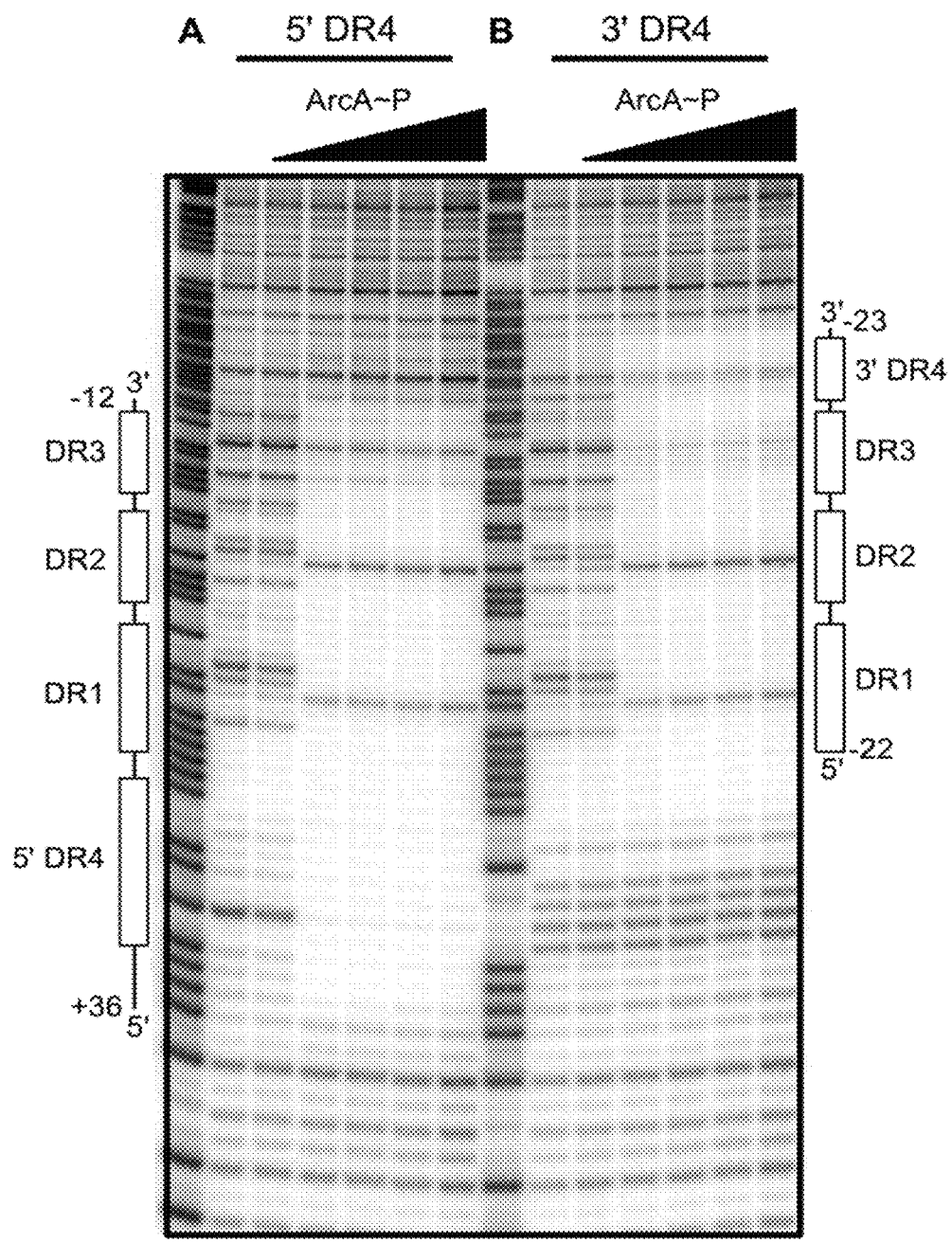
FIG. 4 presents DNase I footprinting of ArcA-P's binding to a icdA promoter region comprising four DR elements. (A) Fourth DR element (5'-TGTTA-3') (SEQ ID NO:2) located 5' of DR1; (B) fourth DR element (5'-TGTTA-3') (SEQ ID NO:2) located 3' of DR3. The regions protected by ArcA-P are indicated with vertical lines, with DR elements indicated by open boxes. The numbers indicate positions relative to the previously determined transcription start site. Samples were electrophoresed with Maxam-Gilbert ladders (A+G) made using the same DNA (lane 1). ArcA-P protein concentrations are given from left to right in nM total ArcA-P protein as follows: 0, 50, 150, 300, 600, and 1,000 nM.

Although our DNase I footprinting analysis suggests that an ArcA-P dimer bound to DR1 and DR2 stabilizes the binding of ArcA-P to DR3, whether ArcA-P binds as a dimer or as a monomer to DR3 is an open question. The lack of DNase I protection of the DNA sequence adjacent to DR3 suggests that if a dimer is bound, then this sequence either contributes only weakly or not at all to stabilizing the binding of the second dimer. To determine whether adding a fourth DR element facilitates ArcA-P binding and increases the footprint length, a consensus DR element (5'-TGTTA-3') (SEQ ID No:2) was added at the same spacing (11 bp center-to-center) to either the 3' or the 5' end of the three-DR ArcA binding site within the icdA promoter region and DNase I footprinting experiments were performed. For both variants, the ArcA-P footprint encompassed all four DR elements, and the apparent ArcA-P DNA binding affinity was noticeably increased compared to that with the wt binding site (FIGS. 4A-B). In addition, protection of the entire four-DR site occurred over a very narrow increase in ArcA-P levels (<4-fold), suggesting that cooperativity was also enhanced. Notably, the hypersensitive sites at positions +8 and +19 were unaffected by binding to a fourth repeat, suggesting bending or kinking similar to that with the wt binding site. Finally, as with the wt icdA fragment, binding depended on phosphorylation, since no binding was observed with unphosphorylated ArcA at protein concentrations up to 1 µM (data not shown).

Despite the potential for enhancement of DNA binding, multiple consecutive high-information-content DR sites are relatively rare in the E. coli genome (Park et al., *PLoS One Genetics* 9:e1003839 (2013)), raising the question of whether there is a tradeoff between DNA binding and the ability to respond to the regulatory signal. To test whether the $P_{1icdA}$ variant with four consecutive DR binding sites still retains $O_2$-dependent regulation, we measured β-galactosidase activity produced from a P1icdA-lacZ transcriptional fusion containing either the 3' or the 5' DR4 element and compared it to that produced with the wt promoter under anaerobic or aerobic conditions. As expected, ArcA-dependent repression of wt $P_{1icdA}$ was largely relieved in the presence of $O_2$ (FIG. 3C), consistent with the known reduction in ArcA-P levels under aerobic conditions (Rolfe et al., *J. Biol. Chem.* 286:10147-10154 (2011)). However, addition of DR4 to the 5' end not only resulted in an 8-fold increase in repression compared to the repression with the wt binding site under anaerobic conditions (FIG. 3B) but also increased repression by ArcA under aerobic conditions to nearly the same magnitude observed under anaerobic conditions, indicating that ArcA repression of this variant site was no longer $O_2$ sensitive (FIG. 3C). The addition of DR4 to the 3' end disrupted promoter function, preventing assessment of ArcA repression (data not shown). The simplest interpretation of these results is that strengthening binding affinity disrupts $O_2$-dependent regulation of ArcA DNA binding. We also tested whether the degeneracy of DR2 and DR3 (FIG. 1C) is important for maintaining $O_2$-dependent regulation of $P_{1icdA}$ by assaying the variants where the sites were mutated toward the consensus. Improving DR2 or DR3 toward the consensus also increased aerobic $P_{1icdA}$ repression compared to that with the wild-type binding site, but the effect was more pronounced with a consensus DR3 element (~2.5-fold versus 7-fold repression) (FIG. 3C). $P_{1icdA}$ with both consensus DR2 and DR3 elements was even more repressed by ArcA under aerobic conditions (21-fold) than with either consensus site alone, suggesting that there was an additive effect (FIG. 3C). Together, these results suggest that improving binding affinity through the use of consensus DR elements disrupts the signal-dependent regulation of ArcA DNA binding, suggesting that the degeneracy of DR2 and DR3 is important for balancing anaerobic repression with $O_2$-dependent relief of repression.

Figure 5:
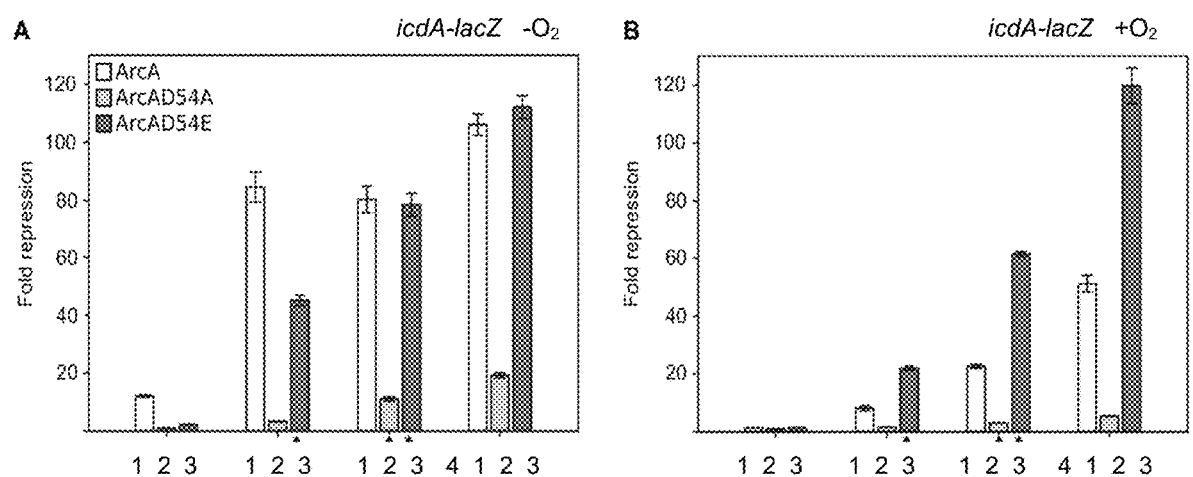
FIG. 5 depicts phosphorylation dependence of ArcA repression of $P_{1icdA}$ in strains with strengthened ArcA binding sites. The fold repression of $P_{1icdA}$-lacZ in strains containing arcA-FRT-cat-FRT (white bars), arcA(D54A)-FRT-cat-FRT (light-gray bars), or arcA(D54E)-FRT-cat-FRT (dark-gray bars) was determined from cells grown under anaerobic (A) or aerobic (B) conditions and calculated by dividing the β-galactosidase activity of a ΔarcA strain by the activity with each of the arcA alleles. Asterisks denote DR elements that have been mutated toward the consensus. Error bars represent the standard errors of results from at least three independent replicates.

To test whether the enhanced repression of $P_1$icdA with mutant ArcA binding sites is still dependent on phosphorylation, the aspartate residue at position 54 (site of phosphorylation) in the chromosomal copy of arcA was mutated to yield either alanine or glutamate, preventing phosphorylation from ArcB. The D54A variant reduced the repression of all $P_{1icdA}$-lacZ constructs compared to that with the wt protein under both aerobic and anaerobic growth conditions (FIG. 5A). This suggests that, independent of the strength of the binding site, repression is largely dependent on the phosphorylated form of ArcA. This result is consistent with the failure of unphosphorylated ArcA to bind to the four DR sites in vitro (data not shown). Thus, the elevated aerobic repression with the strengthened ArcA binding sites appears to result from increased occupancy of the small amount of ArcA-P likely present during aerobic conditions.

We expected ArcA(D54E) to similarly reduce the repression of P1icdA, since this substitution has previously been shown to prevent both phosphorylation from ArcB and binding to the pfl promoter. Surprisingly, ArcA(D54E) still strongly repressed $P_1$icdA constructs with strengthened binding sites even though repression of wt $P_1$icdA was largely eliminated; repression of the construct with a consensus DR3 element was reduced by only 2-fold, while repression of constructs with consensus DR2 and DR3 elements or a fourth DR element was indistinguishable from that observed with the wt protein under anaerobic conditions (FIG. 5B). Furthermore, under aerobic conditions, ArcA (D54E) repression of P1icdA was increased compared to that of wt ArcA for all binding sites tested (FIG. 5B). Thus, D54E ArcA appears to partially mimic phosphorylated ArcA. An aspartate-to-glutamate substitution has previously been shown to elicit constitutive activity in some response regulators (Smith et al., *Mol. Microbiol.* 51:887-901 (2004)).

Discussion. The results presented here provide new insight into the plasticity of the DNA elements that can control transcriptional repression. Our data suggest that for icdA, the arrangement of multiple DNA binding elements is be tailored to achieve both sufficient DNA binding affinity and repression by ArcA while maintaining $O_2$-dependent regulation. We propose that the distribution of DNA binding information across several DR elements may be a design principle to achieve the appropriate level of repression and to tune the signal-dependent regulation of target genes for both ArcA and other repressors.

Our analysis of the three DR elements of the icdA promoter indicates that ArcA-P binding to the lowest-information-content site, DR3, is stabilized by ArcA-P bound to DR1 and DR2, suggestive of a cooperative DNA binding mechanism. The lack of an observable defect in binding to DR1 or DR2 when DR3 was eliminated suggests that the cooperative energy is predominantly partitioned toward binding of DR3, as expected for sites with large differences in intrinsic levels of binding energy (Ackers et al., *J. Mol. Biol.* 170:223-242 (1983)). Since ~67 genomic sites have an odd number of DR elements (Park et al., *PLoS One Genetics* 9:e1003839 (2013)), cooperativity is likely an important determinant for ArcA binding genome-wide.

Figure 6:
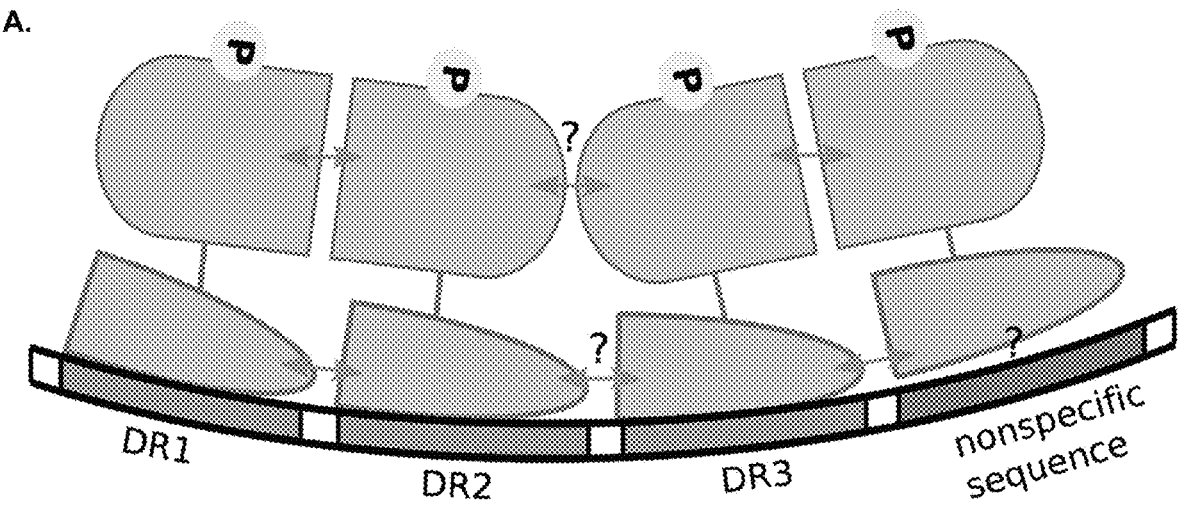
FIG. 6 presents a model for ArcA-P binding to a three-DR binding site. The orientation and protein-protein contacts between the N- and C-terminal domains within an ArcA-P dimer are based on crystallographic data from ArcA and PhoB, respectively (Toro-Roman et al., *J Mol Biol* 349:11-26 (2005); Blanco et al., *Structure* 10:701-713 (2002)). Energetically favorable contacts are indicated in blue, while contacts likely to be less favorable are indicated in red. We propose that two ArcA-P dimers bind to a three-DR site in a cooperative manner; the first dimer binds to DR1 and DR2, and a second dimer binds to DR3 and adjacent nonspecific sequences. A favorable energetic contribution from the interaction between ArcA-P dimers is likely required to overcome the poor binding affinity of an ArcA-P dimer to DR3 and adjacent nonspecific sequence. Alternatively, it is possible that dimerization is not required for binding to DR3; ArcA-P may bind to DR3 as a monomer. Potential regions of interaction between ArcA-P molecules in both scenarios are marked with question marks.
Figure 6:
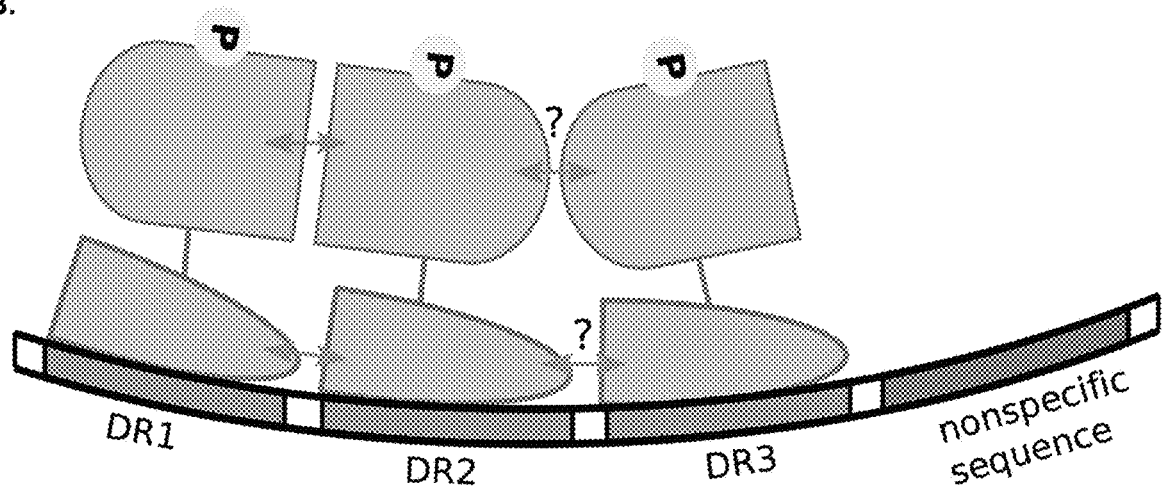

The stoichiometry of ArcA-P binding to DR1, -2, and -3 remain unclear. It is possible that ArcA-P binds to the icdA promoter as a dimer of dimers; one dimer binds DR1 and DR2, as depicted in the PhoB and KdpE DNA cocrystal structures (Blanco et al., *Structure* 10:701-713 (2002); Narayanan et al., *Nat. Commun.* 5:3282 (2014)), and the second dimer binds DR3 but only weakly to adjacent DNA sequence, such that no footprint is observed (FIG. 6A). This model is supported by the requirement for phosphorylation of ArcA to bind to DR3, which is also known to promote dimer formation among OmpR/PhoB response regulators (Mack et al., *J. Mol. Biol.* 389:349-364 (2009); Barbieri et al., *J. Mol. Biol.* 425:1612-1626 (2013)). However, phosphorylation may simply eliminate an interaction between the regulatory and DNA-binding domains, allowing ArcA-P to bind as a monomer to DR3 (FIG. 6B). Thus, additional studies are necessary to determine the stoichiometry of ArcA binding to the icdA promoter and whether this stoichiometry is shared among other ArcA sites with three DR elements.

In either scenario, the predominance of three DR sites with 11-bp CTC spacing between each DR in the *E. coli* genome, together with our previous finding that ArcA-P did not bind to a predicted DR3 element in which the CTC spacing was separated by an additional bp (Park et al., *PLoS One Genetics* 9:e1003839 (2013)), suggests that protein-protein interactions between correctly spaced subunits is important for cooperative ArcA binding to multiple DRs. Because the C-terminal domain of ArcA binds as a dimer to two adjacent DRs, one can envision that binding of an ArcA-P dimer to DR1 and -2 stabilizes a second dimer or a monomer via protein interactions with DR3. Additionally, the hypersensitive site observed when all three (or four) DR elements of icdA were occupied may indicate a requirement for DNA bending to facilitate these protein-protein interactions.

At icdA, the differences in binding affinity of an ArcA-P dimer for DR1/DR2 versus DR3 increases the amount of ArcA-P required for full occupancy in vitro. Assuming that ArcA-P binds the same way in vivo, this binding site architecture would extend the sensitivity to ArcA-P levels by increasing the amount of ArcA-P required for maximal repression. This property may be a feature shared with other response regulators, since in the case of OmpR, the binding of an OmpR-P dimer to box 1 (two DR elements) at the ompF and ompC promoters occurs at a lower concentration of OmpR-P than does binding of OmpR-P to adjacent OmpR boxes ((Yoshida et al., *J. Biol. Chem.* 281:17114-17123 (2006); Rampersaud et al., *J. Biol. Chem.* 269:12559-12566 (1994)). Similarly, binding of PhoB-P to the upstream PhoB box at the pstS promoter occurs at a lower concentration of PhoB-P than when it binds to the adjacent, downstream box (Makino et al., *J. Mol. Biol.* 259:15-26 (1996)).

On the other hand, promoters with three or more DR elements of high information content appear to result in ArcA-P occupancy over a very narrow range of protein concentrations. For example, when the disparity in ArcA-P binding affinities at icdA was reduced by replacing the nonspecific sequence adjacent to DR3 with a fourth DR element, the increase in binding affinity resulted in the promoter bound by ArcA-P in a highly cooperative manner. A similar switch-like occupancy of ArcA-P was also observed for the four DR elements at the astC promoter (Park et al., *PLoS One Genetics* 9:e1003839 (2013)). Data obtained using an icdA-lacZ reporter fusion indicate that strengthening DR3 toward the consensus likely also enhances binding affinity. Indeed, all three DR elements at the acs promoter are bound over a narrow range of ArcA-P levels, likely due to a greater energetic contribution to ArcA-P binding provided by a stronger DR3 element (Park et al., *PLoS One Genetics* 9:e1003839 (2013)). Thus, the combinatorial effect of strong or weak DR elements may be used to either dampen or enhance the concentration-sensitive occupancy by ArcA-P compared to that of a site with only two DRs.

The configuration of the ArcA DR elements may also provide a mechanism for achieving a stepwise response to changes in $O_2$, as suggested for OmpR-P dimer binding to the ompF and ompC promoters in response to changes in osmolarity (Yoshida et al., *J. Biol. Chem.* 281:17114-17123). For example, under aerobic conditions, ArcA-P levels are likely insufficient for appreciable binding to the icdA promoter; thus, icdA expression is high, consistent with the need for isocitrate dehydrogenase for carbon oxidation in the TCA cycle. However, as $O_2$ becomes limiting, ArcA-P levels likely increase (Rolfe et al., *J. Biol. Chem.* 286:10147-54 (2011)), perhaps allowing an ArcA-P dimer to bind DR1 and DR2, reducing icdA expression to an intermediate level. As $O_2$ is further depleted, ArcA-P levels likely increase more, and we expect binding to all three DRs, reducing icdA expression to levels optimal for anaerobic metabolism. Experimental support for this model came from showing that $O_2$-dependent regulation was disrupted at icdA either by adding a fourth DR element or by improving DR2 and DR3. Thus, these results suggest that the degeneracy in DR2 and DR3 and the absence of a recognizable fourth DR element is important for maintaining the balance between strong, but not complete, anaerobic repression and $O_2$-dependent relief of repression.

Given the function of the majority of ArcA-repressed operons in aerobic respiratory metabolism, this balance between high affinity ArcA-P binding and maintenance of $O_2$-dependent regulation is likely widely applicable to genomic ArcA binding sites. Furthermore, it may explain why there are many three-DR sites without identifiable fourth DR elements in the *E. coli* genome and, additionally, why the average strength of DR elements decreases as the number of DR elements in the binding site increases. Nevertheless, both the strength of the promoter and the incorporation of other regulator binding sites should at least partially dictate the specific ArcA binding site architecture required to achieve optimal regulation, with four DR sites apparently necessary at some promoters.

The saturation of ArcA-P binding to DR3 and/or DR4 sites over a narrow range of ArcA-P concentrations in vitro suggests that these promoters may respond to ArcA-P with a switch-like behavior as cells become limited for $O_2$. For the engineered icdA promoter containing a four-DR site, it seems likely that the affinity of ArcA-P for this site is so strong that the concentration of ArcA-P present under aerobic conditions is sufficient to occupy this site so that an $O_2$-dependent change in repression cannot be observed. Nevertheless, our data provide a model for how the ArcA binding site architecture may be optimized to achieve regulatory logic schemes not possible with a canonical two-DR binding site. This plasticity in the promoter architecture likely plays an important role in linking the redox-sensing properties of the ArcAB two-component system with the fine-tuning of expression of carbon oxidation pathway levels.

The incorporation of plasticity in the binding site architectures that we observed for ArcA may be a common regulatory strategy for other global transcriptional repressors (e.g., Fur, LexA). Like ArcA, Fur binding sites are variable in length (30 to 103 bp) and contain multiple Fur recognition elements of differing predicted strengths and locations with respect to the promoter elements (Chen et al., Nucleic Acids Res. 35:6762-77 (2007)). Although the physiological basis for this plasticity is unknown, it may similarly impose a differential sensitivity of regulatory target expression to changes in Fe-Fur concentrations. Furthermore, although LexA-regulated genes typically have only one LexA binding site, differences in the strengths and locations of these sites alter the absolute level and sensitivity of expression (Butala et al., Cell. Mol. Life Sci. 66:82-93 (2009)). In a few cases, adjacent LexA sites are bound in a cooperative manner, further enhancing the sensitivity to changes in signal, as hypothesized for the ArcA binding sites located upstream of acs and astC. Given the conserved dimerization mode and binding of direct repeat DNA sites among response regulators within the OmpR/PhoB family (Toro-Roman et al., J. Mol. Biol. 349:11-26 (2005)), this architectural plasticity may be a common regulatory strategy, particularly for regulators that act as repressors at many targets.

Methods and Materials

Strain construction—An icdA-promoter-lacZ fusion was constructed as described previously (Kang et al., J. Bacteriol. 187:1135-1160 (2005)) by amplifying the region from −50 to −330 with respect to the start of translation using primers flanked by XhoI or BamHI restriction sites. The icdA fragment contains two promoters: one whose expression is dependent on ArcA ($P_1$) and a second promoter whose expression is dependent on FruR (P2) (Chao et al., J. Bacteriol. 179:4299-4304 (1997); Prost et al., J. Bacteriol. 181:893-898 (1999)). To examine icdA expression from only $P_1$, transcription from $P_2$ was eliminated using QuikChange site-directed mutagenesis (Stratagene) as described previously (Nesbit et al., J. Mol. Biol. 387-28-41 (2009)) to mutate the −10 site from 5'-CATTAT-3' to 5'-CGGTGA-3', generating pPK9476. Mutations within the ArcA-binding site of the icdA promoter were similarly generated using pPK9476 as a template (mutations are numbered with respect to $P_1$ in Table 3). These lacZ promoter constructs were then recombined into the chromosomal lac operon as previously described (Kang et al., J. Bacteriol. 187:1135-1160 (2005)) and then transduced using P1 vir into MG1655 and PK9416 to form the strain derivatives listed in Table 1.

TABLE 3

Strains and Plasmids

| Strain/Plasmid | Relevant genotype | Source |
|---|---|---|
| strains | | |
| MG1655 | F−, λ −, rph-1 | Kiley Laboratory |
| PK9416 | MG1655 ΔarcA | Park et al., PLoS Genetics 9: e1003839 (2013) |
| PK9483 | MG1655 PicdA(-58GGTGA-54)-lacZ | Park et al. (2013) |
| PK9484 | PK9416 PicdA(-58GGTGA-54)-lacZ | Park et al. (2013) |
| PK9494 | MG1655 PicdA(-58GGTGA-54, 19TG20)-lacZ | This study |
| PK9495 | PK9416 PicdA(-58GGTGA-54, 19TG20)-lacZ | This study |
| PK9486 | MG1655 PicdA(-58GGTGA-54, 8TG9)-lacZ | This study |
| PK9487 | PK9416 PicdA(-58GGTGA-54, 8TG9)-lacZ | This study |
| PK9496 | MG1655 PicdA(-58GGTGA-54, -4TG-3)-lacZ | This study |
| PK9497 | PK9416 PicdA(-58GGTGA-54, -4TG-3)-lacZ | This study |
| PK9915 | MG1655 PicdA(-58GGTGA-54, 29AACA32)-lacZ | This study |
| PK9916 | PK9416 PicdA(-58GGTGA-54, 29AACA32)-lacZ | This study |
| PK9917 | MG1655 PicdA(-58GGTGA-54, -15ACA-13)-lacZ | This study |
| PK9918 | PK9416 PicdA(-58GGTGA-54, -15ACA-13)-lacZ | This study |
| PK9924 | MG1655 PicdA(-58GGTGA-54, -5A)-lacZ | This study |
| PK9925 | PK9416 PicdA(-58GGTGA-54, -5A)-lacZ | This study |
| PK9941 | MG1655 PicdA(-58GGTGA-54, 7A)-lacZ | This study |
| PK9942 | PK9416 PicdA(-58GGTGA-54, 7A)-lacZ | This study |
| PK9943 | MG1655 PicdA(-58GGTGA-54, 7A, -5A)-lacZ | This study |
| PK9944 | PK9416 PicdA(-58GGTGA-54, 7A, -5A)-lacZ | This study |
| PK10967 | MG1655 PicdA(-58GGTGA-54, 7A, -4TG-3)-lacZ | This study |
| PK10968 | PK9416 PicdA(-58GGTGA-54, 7A, -4TG-3)-lacZ | This study |
| BW25993 | lac$I^q$ ΔlacZ$_{WJ16}$hsdR5 14 ΔaraBAD$_{AH33}$ ΔrhaBAD$_{LD78}$ | (Datsenko & Wanner, 2000) |
| PK9970 | PK9483 arcA:cat | This study |
| PK9973 | PK9915 arcA:cat | This study |
| PK9971 | PK9924 arcA:cat | This study |
| PK9972 | PK9943 arcA:cat | This study |
| PK9980 | PK9483 arcA-D54A:cat | This study |
| PK9983 | PK9915 arcA-D54A:cat | This study |
| PK9981 | PK9924 arcA-D54A:cat | This study |

TABLE 3-continued

Strains and Plasmids

| Strain/Plasmid | Relevant genotype | Source |
|---|---|---|
| PK9982 | PK9943 arcA-D54A:cat | This study |
| PK9975 | PK9483 arcA-D54E:cat | This study |
| PK9978 | PK9915 arcA-D54E:cat | This study |
| PK9976 | PK9924 arcA-D54E:cat | This study |
| PK9977 | PK9943 arcA-D54E:cat | This study |
| Plasmids | | |
| pKD46 | Phage λ gam-bet-exo genes under ParaB control | Courtesy of B. L. Wanner |
| pKD13 | FRT-kan-FRT | Datsenko and Wanner |
| pKD32 | FRT-cat-FRT | Courtesy of B. L. Wanner |
| pPK7035 | kan gene from pHP45Ω and BamHI-NdeI fragment from pRS1553 into pBR322 | (Kang et al., 2005) |
| pPK9476 | pPK7035 PicdA(-58GGTGA-54)-lacZ | Park et al. (2013) |
| pPK9477 | pPK7035 PicdA(-58GGTGA-54 19TG20)-lacZ | This study |
| pPK9908 | pPK7035 PicdA(-58GGTGA-54 8TG9)-lacZ | This study |
| pPK9909 | pPK7035 PicdA(-58GGTGA-54 -4TG-3)-lacZ | This study |
| pPK9913 | pPK7035 PicdA(-58GGTGA-54 29AACA32)-lacZ | This study |
| pPK9914 | pPK7035 PicdA(-58GGTGA-54 -15ACA-13)-lacZ | This study |
| pPK15001 | pPK7035 PicdA(-58GGTGA-54, 7A, -4TG-3)-lacZ | This study |
| pPK9965 | arcA in pBR322 | This study |
| pPK9966 | BamHI FRT-cat-FRT in pPK9965 | This study |
| pPK9431 | Ap$^r$; His$_6$-arcA cloned into NheI and XhoI sites of pET-21d | Park et al. (2013) |

Chromosomally encoded mutants of arcA in which aspartate at position 54 was substituted with glutamate or alanine were constructed in several steps. First, the arcA open reading frame (codons 1 to 238) was amplified using primers flanked by HindIII and BamHI and cloned into pBR322, generating pPK9965. The cat cassette from pKD32, which has flanking FRT (FLP recognition target) sites, was then cloned into the BamHI site, six bp after the arcA termination codon. The arcA gene on the resulting plasmid, pPK9966, was then mutated using QuikChange (Stratagene) site-directed mutagenesis to create the D54A and D54E mutants. The arcA-cat fragments were PCR amplified using a primer having homology to the region upstream of arcA (5'-GGTAGCAAACATGCAGACCCCGCACATTCTTATCG-3'; SEQ ID NO:33) and a primer having homology to the region downstream of arcA (5'-GCGCCGTTTTTTTTGACGGTGGTAAAGCCGATT-AGTGTAGGCTGGAGCTGCTTC-3'; SEQ ID NO:34), and the DNA was electroporated into BW25993/pKD46. The correct recombinants were selected for chloramphenicol (Cm) resistance, confirmed with DNA sequencing, and then transduced with P1 vir into the desired icdA promoter-lacZ fusion strains (Table 3). Placement of the cat cassette downstream of arcA did not alter ArcA activity as icdA promoter-lacZ activity was comparable to that for the wt arcA$^+$ strain for all binding sites tested (FIGS. 3B-C and FIGS. 5A-B).

Determination of the information content of DR elements: A 10-bp ArcA DR element, PWM, derived from the conservation of bases within aligned DR1 and DR2 elements from 128 sequences bound by ArcA in vivo was used to guide the design of binding site mutations. The information content of each mutant DR element was determined by the scan program (24) and is indicated in bits (FIG. 1C). Greater information content should reflect stronger ArcA binding (24). Sequence walkers were used to visualize how DR elements were evaluated by the PWM. Nucleotides extending upwards represent favorable DNA contacts, while letters extending downward represent unfavorable contacts.

β-galactosidase assays—All strains were grown in MOPS minimal medium (Neidhardt et al., 1974) with 0.2% glucose at 37° C. and sparged with a gas mix of 95% $N_2$ and 5% $CO_2$ (anaerobic) or 70% $N_2$, 5% $CO_2$, and 25% $O_2$ (aerobic). Cells were harvested during mid-log growth ($OD_{600}$ of ~0.3 on a Perkin Elmer Lambda 25 UV/Vis Spectrophotometer). To terminate cell growth and any further protein synthesis, chloramphenicol (final concentration, 20 µg/ml) or tetracycline (final concentration, 10 µg/ml) was added, and cells were placed on ice until assayed for β-galactosidase activity (Miller J H (1972) Experiments in molecular genetics. [Cold Spring Harbor, N.Y.]: Cold Spring Harbor Laboratory). β-Galactosidase assays were repeated at least three times and fold repression was calculated by dividing the β-galactosidase activity of a ΔarcA strain by the activity of an arcA$^+$ strain. Standard errors for data plotted as 'fold repression' were calculated using a propagation of standard error formula (Ku, J. Res. National Bureau of Standards 70C:263-273 (1966)).

Overexpression and purification of His$_6$-ArcA—E. coli BL21(DE3) plysS, containing PK943 was grown at 37° C. until an $OD_{600}$ of ~0.4 was reached. A final concentration of 1 mM isopropyl-1-thio-β-d-galactopyranoside (IPTG) was added, and cells were incubated at 30° C. Cells were harvested, suspended in 5 mM imidazole buffer containing 20 mM Tris-Cl (pH 7.9) and 0.5 M NaCl, and lysed by sonication. His$_6$-ArcA was isolated from cell lysates by passing over a Ni-NTA column pre-equilibrated with the 5 mM imidazole, washing extensively with the same buffer followed by 20 and 50 mM imidazole washes, and then eluting with 100 mM imidazole. Fractions containing the overexpressed His$_6$-ArcA, determined by electrophoresis, were dialyzed against 50 mM Tris-Cl, pH 7.5, 0.1 mM DTT, 0.1 mM EDTA, and 0.2 M NaCl. The His$_6$-tag was removed from ArcA by overnight incubation with tobacco etch virus (TEV) protease at 4° C. and passage over a Ni-NTA-agarose column (Qiagen). The protein concentration of ArcA (reported here as monomers) was determined as previously described.

DNase I footprinting: icdA promoter fragments were isolated from pPK9476, pPK9477, pPK9908, pPK9909, pPK9913, pPK9914, and pPK15001 after digestion with XhoI and BamHI. Sequenase Version 2.0 (USB Scientific) was used to 3' radiolabel the BamHI end of the fragment with [$\alpha$-$^{32}$P]-dGTP (PerkinElmer). Labeled DNA fragments were isolated from a non-denaturing 5% acrylamide gel and were subsequently purified with Elutip-d™ columns (Schleicher and Schuell). ArcA was phosphorylated by incubating with 50 mM disodium carbamyl phosphate (Sigma Aldrich) in 50 mM Tris, pH 7.9, 150 mM NaCl, and 10 mM MgCl$_2$ for 1 hour at 30° C. (Lynch & Lin, *J. Bacteria* 178:6238-6249 (1996)) and immediately used in the binding assays. Footprinting assays were performed by incubating phosphorylated ArcA with labeled DNA (~5 nM) for 10 minutes at 30° C. in 40 mM Tris (pH 7.9), 30 mM KCl, 100 µg/ml BSA and 1 mM DTT followed by the addition of 2 µg/ml DNase I (Worthington) for 30 seconds. The DNase I reaction was terminated by the addition of sodium acetate and EDTA to final concentrations of 300 mM and 20 mM, respectively. The reaction mix was ethanol precipitated, resuspended in urea loading dye, heated for 60 seconds at 90° C., and loaded onto a 7 M urea, 8% polyacrylamide gel in 0.5×TBE buffer. An A+G ladder was made by formic acid modification of the radiolabeled DNA, followed by piperidine cleavage (Maxam & Gilbert, Methods Enzymol. 65:499-560 (1980)). The reaction products were visualized by phosphorimaging.

Example 2

Figure 7:
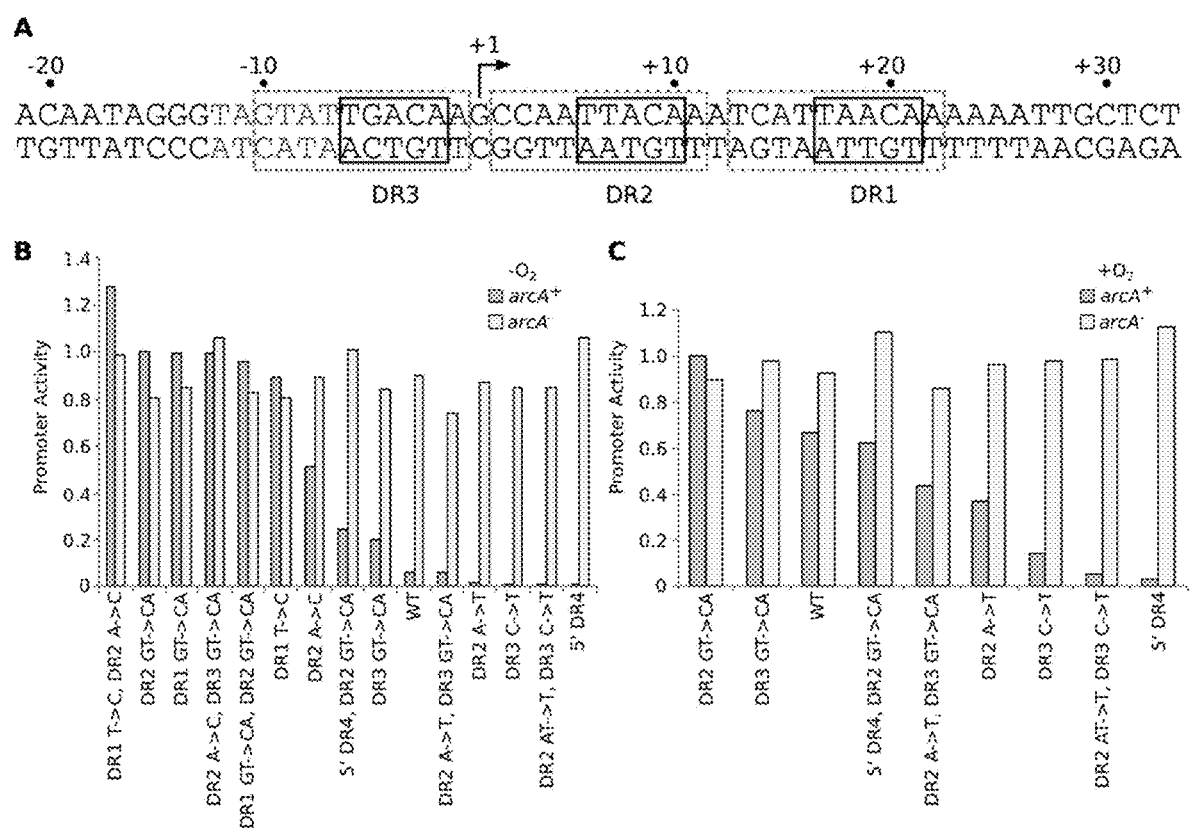
FIG. 7 illustrates (A) the regulatory region of the primary icdA promoter ($P_1$) from *Escherichia coli* (*E. coli*) (SEQ ID NO:17) and modified icdA promoter activity under anaerobic (B) and aerobic (C) conditions. This region is used in the examples as a model for the operation of the set of regulatory regions associated with promoters that are modulated by the ArcAB system. (A) The arrow indicates the position of the previously mapped transcription start site (Chao et al., *J. Bacteriol.* 179:4299-4304 (1997)) with the $\sigma^{70}$-RNA polymerase (RNAP)-10 promoter element bolded. Each of three 10 bp direct repeat (DR) elements in the ArcA binding site associated with the icdA promoter are indicated by dashed grey boxes with the most conserved 5 bp 5'-TGTTA-3' region within each DR element indicated with a solid black box. Modulation of expression from the icdA promoter over a range of activities under both anaerobic (B) and aerobic (C) conditions by mutation of the ArcA binding site associated with the icdA promoter. Strains containing variants of a $P_{1icdA}$ promoter-lacZ fusion construct ($P_{1icda}$-lacZ) were grown in minimal medium with 0.2% glucose. A promoter activity of 1 is defined as the level of $P_{1icda}$-lacZ expression in an *E. coli* mutant having a GT->CA mutation in the second direct repeat (DR2) of the icdA regulatory region that abolished ArcA binding in vitro and repression in vivo. Activity of the remaining mutant promoters is depicted as a fraction of the expression level in this mutant. $P_{1icda}$-lacZ expression in the mutant was equivalent under anaerobic and aerobic conditions.

Modulating ArcA Binding Site Architectures to Modulate Sensitivity of ArcA Repression to Experimental Conditions that Alter ArcA-P Levels The regulatory region of the icdA P$_1$ promoter from *E. coli* comprises the previously mapped transcription start site (Chao et al., 1997), with the $\sigma^{70}$-RNAP −10 promoter element bolded, and three 10 bp DR elements. These DR elements are indicated in FIG. 7A by dashed grey boxes, with the most conserved 5-bp 5'-TGTTA-3' region within each DR element indicated with a solid black box. Modulation of icdA promoter expression over a range of activities under both anaerobic (FIG. 7B) and anaerobic (FIG. 7C) conditions by mutation of the ArcA binding site is shown. P$_1$icdA-lacZ expression in a DR2 GT->CA mutant that abolished ArcA-P binding in vitro and repression in vivo is equivalent to a promoter activity of one. Activity of the remaining mutant promoters is depicted as a fraction of the expression in this DR GT->CA mutant. It should be noted that P$_1$icdA-lacZ expression in a DR GT->CA mutant was equivalent under both anaerobic and aerobic conditions.

Figure 8:
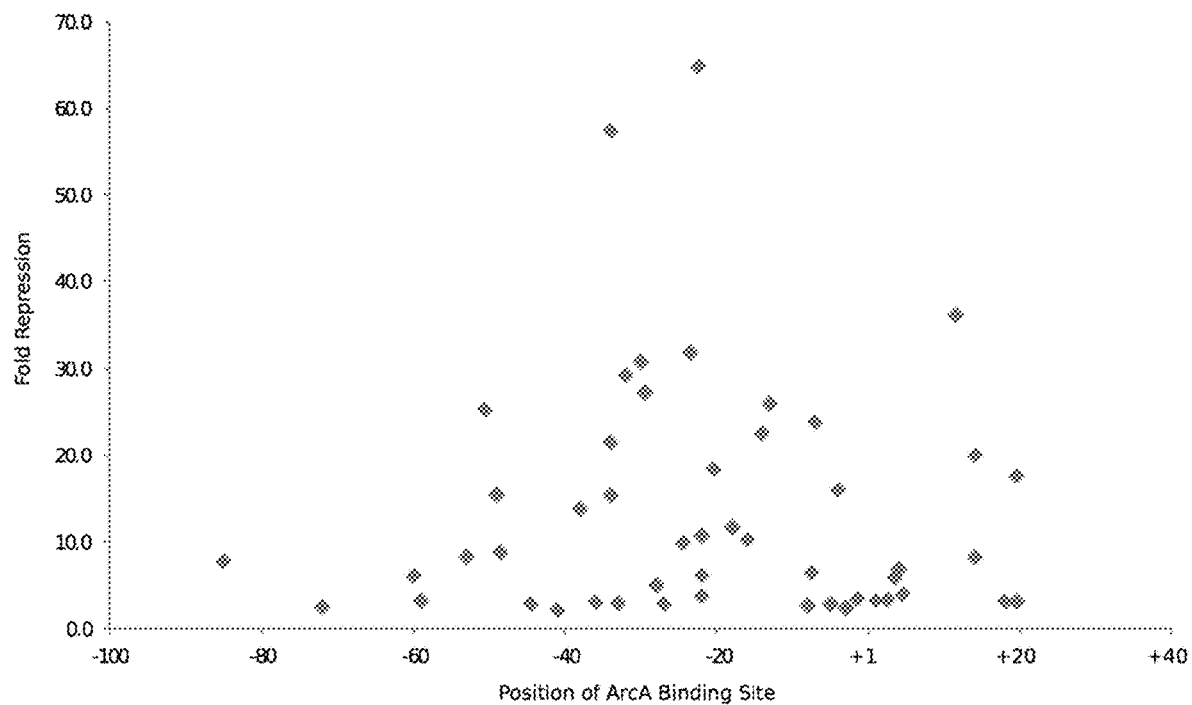
FIG. 8 relates ArcA binding site locations to ArcA-dependent repression. Binding site location was defined as the distance between the experimentally determined transcription start site (TSS) and the midpoint coordinate of each ArcA binding site. Fold repression was calculated by dividing the β-galactosidase activity of a ΔarcA strain by the activity of an arcA$^+$ strain.

In addition to modulating absolute anaerobic or aerobic expression, the different ArcA binding site architectures also can also modulate the sensitivity of ArcA repression to experimental conditions that alter ArcA-P levels (e.g., change in O$_2$ concentration, NADH/NAD$^+$ ratio, etc). (FIG. 8.)

Concentration-sensitive binding of ArcA-P to the *E. coli* icdA promoter was determined using different ArcA binding site architectures. Densiometric analysis of DNase I footprints was used to quantify ArcA-P binding at the icdA promoter. Fractional protection (f) was calculated for each lane:

$$f = 1 - \left\{ \frac{(D_n, \text{site}/D_n, \text{std})}{(D_r, \text{site}/D_r, \text{std})} \right\}$$

where $D_{n,site}$ is the density of lane n within the protected region, $D_{n,std}$ is the density of lane n within a standard, unprotected region above and below the footprinted region, $D_{r,site}$ is the density of the reference (no ArcA-P) lane within the protected region and $D_{r,std}$ is the density of the reference lane within the standard regions.

The data for each ArcA binding site was fit to the four-parameter logistic function (SigmaPlot v. 12.0):

$$y = \min + \frac{(\max - \min)}{1 + \left(\frac{[ArcA-P]}{Kd}\right)^{-n}}$$

where min is the fractional protection with no ArcA-P bound (~0), max is the fractional protection at the highest ArcA-P concentration (~1) and n is the Hill coefficient.

Figure 9:
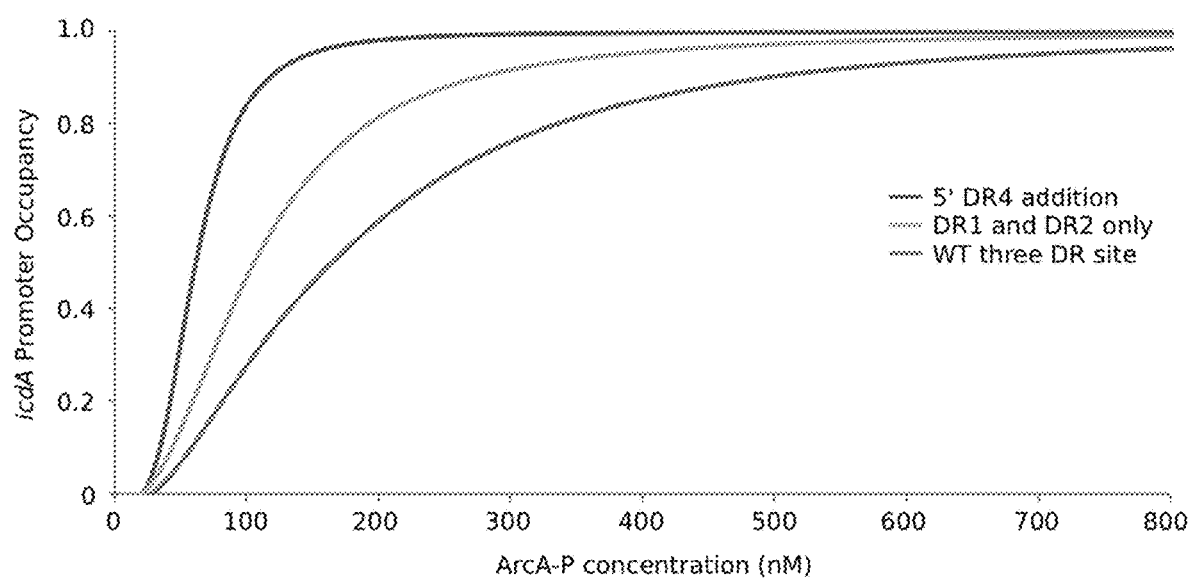
FIG. 9 plots concentration-sensitive binding of the active form of ArcA (phosphorylated ArcA or "ArcA-P") to the icdA promoter having various ArcA binding site architectures. Binding curves were generated by quantifying ArcA-P binding to all three DR elements at the wt icdA promoter, all four DR elements in the 5' DR4 variant, and DR1 and DR2 in the DR3 GT->CA variant. ArcA-P binding at the icdA promoter was quantified by densiometric analysis of DNase I footprints.

The curve for the WT three DR site represents a combination of the binding isotherms for an ArcA-P dimer to DR1 and DR2 and to DR3 (and perhaps sequence adjacent to DR3) (FIG. 9). In this case, a promoter occupancy of one represents binding to all three DR elements while an occupancy of 0.5 represents binding to just DR1 and DR2 (half of the site).

Figure 10:
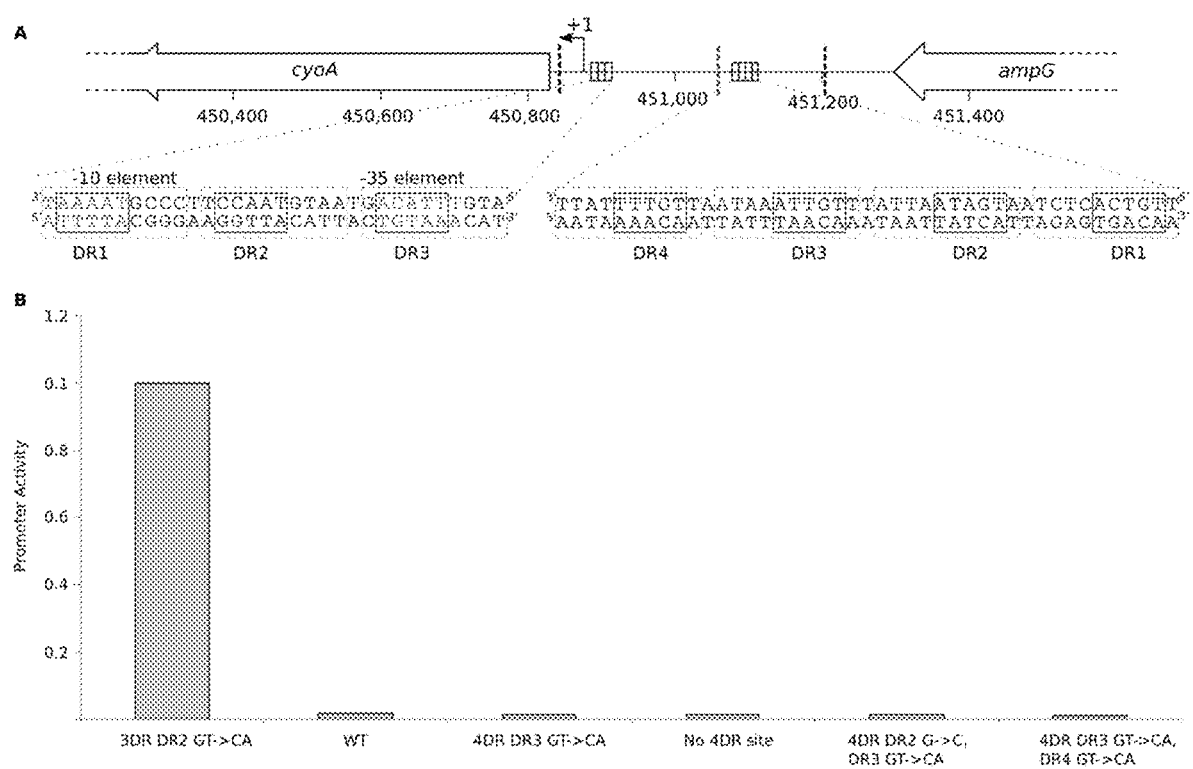
FIG. 10 presents ArcA binding site mutation data with a cyoA-promoter-lacZ fusion. (A) The top strand is the coding strand and the two ArcA binding sites (rectangles) (SEQ ID NOS:40 and 41) are directionally oriented on opposite strands. (B) Weakening the three downstream DRs that overlap the −10 and −35 elements resulted in complete loss of ArcA-dependent repression. A slight increase in ArcA-dependent repression was observed when the upstream four DRs were weakened via mutation or eliminated via a shortened cyoA-promoter-lacZ fusion.

The role of two upstream ArcA binding sites in the regulation of cyo expression was investigated using β-galactosidase assays. The two predicted ArcA binding are indicated by black rectangles in FIG. 10A. The first binding site contains three DRs and overlaps the −10 and −35 elements while the second contains four DRs and is located ~200 bp upstream. The top strand is the coding strand and the two ArcA binding sites are directionally oriented on opposite strands. The 10-bp DR elements are indicated by dashed grey boxes with the most conserved 5-bp 5'-TGTTA-3' region within each DR element indicated with a solid black box. The cyo promoter was fused to lacZ (promoter region indicated with dark broken lines; +26 to −329 with respect to the TSS) and each of the ArcA binding sites were systematically weakened through mutagenesis. A shorter cyoA-promoter-lacZ fusion (lighter broken line; +26 to −179 with respect to the TSS) that does not include the upstream DR4 element was also generated (FIG. 10A). Weakening the more downstream three DRs that overlap the −10 and −35 elements resulted in complete loss of ArcA-dependent repression, suggesting that this binding site is essential for anaerobic repression of the cyo operon (FIG. 10B). In contrast, when the upstream four DRs was weakened through mutation or completely eliminated through use of a shortened cyoA-promoter-lacZ fusion, a slight increase in ArcA-dependent repression was observed (FIG. 10B). Therefore, this binding site is not required for anaerobic repression and may instead partially disrupt repression at the downstream three DRs. ArcA repression is abolished in all constructs under aerobic conditions (data not shown).

We claim:

1. A vector comprising a synthetic gene switch comprising
   (i) a first sequence determinant portion selected from the group consisting of SEQ ID NOs:2, 4, 36, 37, 38, and 39;
   (ii) a second sequence determinant portion selected from the group consisting of SEQ ID NOs:2, 4, 36, 37, 38, and 39; and
   (iii) a third sequence determinant portion selected from the group consisting of SEQ ID NOs:2, 4, 36, 37, 38, and 39, wherein the first and second sequence determinant portions are separated by an 11-basepair center-to-center spacing interval, the second and third sequence determinant portions are separated by an 11-basepair center-to-center spacing interval, and the first and third sequence determinant portions are separated by a 22-basepair center-to-center spacing interval, and with the proviso that if the first sequence determinant portion is SEQ ID NO:2, the second sequence determinant portion is SEQ ID NO:37, and the third sequence determinant portion is SEQ ID NO:39 the synthetic gene switch additionally comprises a fourth sequence determinant portion selected from the group consisting of SEQ ID NOs:2, 4, 36, 37, 38, and 39, wherein the synthetic gene switch is operably linked to a promoter.

2. The vector of claim 1, wherein the synthetic gene switch is positioned with respect to the promoter on the vector to confer ArcA-dependent promoter activity.

3. A bacterial host cell comprising the vector of claim 1.

4. The bacterial host cell of claim 3, wherein the cell is an *E. coli* cell.

5. The vector of claim 1, wherein the synthetic gene switch comprises a sequence selected from the group consisting of SEQ ID NOs:5-16.

6. The vector of claim 5, wherein the synthetic gene switch comprises a sequence selected from the group consisting of SEQ ID NOs:18-32.

7. An expression vector comprising,
a synthetic gene switch comprising:
(i) a first sequence determinant portion selected from the group consisting of SEQ ID NOs:2, 4, 36, 37, 38, and 39;
(ii) a second sequence determinant portion selected from the group consisting of SEQ ID NOs:2, 4, 36, 37, 38, and 39; and
(iii) a third sequence determinant portion selected from the group consisting of SEQ ID NOs:2, 4, 36, 37, 38, and 39,
wherein the first and second sequence determinant portions are separated by an 11-basepair center-to-center spacing interval, the second and third sequence determinant portions are separated by an 11-basepair center-to-center spacing interval, and the first and third sequence determinant portions are separated by a 22-basepair center-to-center spacing interval, and with the proviso that if the first sequence determinant portion is SEQ ID NO:2, the second sequence determinant portion is SEQ ID NO:37, and the third sequence determinant portion is SEQ ID NO:39, the synthetic gene switch additionally comprises a fourth sequence determinant portion selected from the group consisting of SEQ ID NOs: 2, 4, 36, 37, 38, and 39,
wherein the synthetic gene switch additionally comprises at least a portion of an RNA polymerase binding site; and
a target nucleic acid sequence downstream of the synthetic gene switch.

8. The expression vector of claim 7, wherein the synthetic gene switch is operably linked to a promoter.

9. A bacterial host cell comprising the vector of claim 7.

10. The bacterial host cell of claim 9, wherein the cell is an *E. coli* cell.

11. The expression vector of claim 7, wherein the synthetic gene switch comprises a fourth sequence determinant portion selected from the group consisting of SEQ ID NOs:2, 4, 36, 37, 38, and 39 and wherein the fourth sequence determinant portion is separated from either the first or third sequence determinant portions by an 11-basepair center-to-center spacing interval.

12. The expression vector of claim 7, wherein the RNA polymerase binding site is a binding site for bacterial $\sigma^{70}$-RNA polymerase.

13. The vector of claim 7, wherein the synthetic gene switch comprises a sequence selected from the group consisting of SEQ ID NOs:5-16.

14. The vector of claim 13, wherein the synthetic gene switch comprises a sequence selected from the group consisting of SEQ ID NOs:18-32.

15. A method for modulating gene expression of a target nucleic acid sequence, the method comprising:
introducing into a host cell an expression vector of claim 7; and
subjecting the host cell to a change in oxygen concentration until the gene expression level of the target nucleic acid sequence is modulated.

16. The method of claim 15, wherein the gene expression level is modulated under anaerobic conditions.

17. An expression vector comprising,
a synthetic gene switch comprising:
(i) a first sequence determinant portion selected from the group consisting of SEQ ID NOs:2, 4, 36, 37, 38, and 39;
(ii) a second sequence determinant portion selected from the group consisting of SEQ ID NOs:2, 4, 36, 37, 38, and 39; and
(iii) a third sequence determinant portion selected from the group consisting of SEQ ID NOs:2, 4, 36, 37, 38, and 39,
wherein the first and second sequence determinant portions are separated by an 11-basepair center-to-center spacing interval, the second and third sequence determinant portions are separated by an 11-basepair center-to-center spacing interval, and the first and third sequence determinant portions are separated by a 22-basepair center-to-center spacing interval, and with the proviso that if the first sequence determinant portion is SEQ ID NO:2, the second sequence determinant portion is SEQ ID NO:37, and the third sequence determinant portion is SEQ ID NO:39, the synthetic gene switch additionally comprises a fourth sequence determinant portion selected from the group consisting of SEQ ID NOs: 2, 4, 36, 37, 38, and 39,
wherein the synthetic gene switch comprises a promoter element; and
a target nucleic acid sequence downstream of the synthetic gene switch.

18. The vector of claim 17, wherein the synthetic gene switch comprises a sequence selected from the group consisting of SEQ ID NOs:5-16.

19. The vector of claim 18, wherein the synthetic gene switch comprises a sequence selected from the group consisting of SEQ ID NOs:18-32.

20. A bacterial host cell comprising the vector of claim 17.

21. The bacterial host cell of claim 20, wherein the cell is an *E. coli* cell.

* * * * *